United States Patent
Chang et al.

(10) Patent No.: US 10,071,093 B2
(45) Date of Patent: *Sep. 11, 2018

(54) METHOD OF TREATING PARKINSON'S DISEASE WITH A DIARYLMETHYLPIPERAZINE COMPOUNDS EXHIBITING DELTA OPIOID RECEPTOR AGONIST ACTIVITY

(71) Applicant: VERSI GROUP, LLC, Gladstone, NJ (US)

(72) Inventors: Kwen-Jen Chang, Chapel Hill, NC (US); William Pendergast, Durham, NC (US); Jonathon D. S. Holt, Durham, NC (US)

(73) Assignee: VERSI GROUP, LLC, Gladstone, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/634,262

(22) Filed: Jun. 27, 2017

(65) Prior Publication Data
US 2017/0290823 A1 Oct. 12, 2017

Related U.S. Application Data

(60) Continuation of application No. 14/170,791, filed on Feb. 3, 2014, now Pat. No. 9,701,645, which is a division of application No. 11/470,012, filed on Sep. 5, 2006, now Pat. No. 8,642,599.

(60) Provisional application No. 60/714,187, filed on Sep. 2, 2005.

(51) Int. Cl.
| | |
|---|---|
| *A61K 31/497* | (2006.01) |
| *A61K 31/495* | (2006.01) |
| *A61K 31/496* | (2006.01) |
| *A61K 45/06* | (2006.01) |
| *C07D 241/04* | (2006.01) |
| *A61K 9/70* | (2006.01) |

(52) U.S. Cl.
CPC .......... *A61K 31/495* (2013.01); *A61K 9/7023* (2013.01); *A61K 31/496* (2013.01); *A61K 45/06* (2013.01); *C07D 241/04* (2013.01)

(58) Field of Classification Search
CPC combination set(s) only.
See application file for complete search history.

(56) References Cited

U.S. PATENT DOCUMENTS

| | | |
|---|---|---|
| 6,875,772 B2 | 4/2005 | Neustadt et al. |
| 7,253,173 B2 | 8/2007 | Brown et al. |
| 2002/0052007 A1 | 5/2002 | Chang et al. |
| 2003/0144299 A1 | 7/2003 | Chang et al. |

FOREIGN PATENT DOCUMENTS

WO    WO2005/053703    6/2005

OTHER PUBLICATIONS

Broom, D.C. et al. (2002) Nonpeptidic delta-opioid receptor agonists reduce immobility in the forced swim assay in rats. *Neuropsychopharmacology* 26(6):744-755.
Cassano, P. et al. (2004) Pramipexole in Treatment-Resistant Depression: An Extended Follow-up. *Depression and Anxiety* 20:131-138.
Chang, K.J. et al. (1993) A novel, potent and selective nonpeptidic delta opioid receptor agonist BW373U86. *J Pharmacol Exp Ther* 267(2):852-857.
Comer, S.D. et al. (1993) Convulsive effects of systemic administration of the delta opioid agonist BW373U86 in mice. *J Pharmacol Exp Ther* 267(2):888-895.
Cuello, C.A. et al. (1978) Evidence for a long leu-enkephalin striopallidal pathway in rat brain. *Nature* 271:178-180.
De Ceballos, M.L. et al. (1993) Parallel alterations in Met-enkephalin and substance P levels in medial globus pallidus in Parkinson's disease patients. *Neurosci. Lett.* 160:163-166.
Gerfen, C.R. et al. (1988) Distribution of striatonigral and striatopallidal peptidergic neurons in both patch and matrix compartments: An in situ hybridization histochemistry and fluorescent retrograde tracing study. *Brain Res.* 460:161-167.
Henry, B. et al. (1996) Potential of opioid antagonists in the treatment of levodopa-induced dyskinesias in Parkinson's disease. *Drugs Aging* 9:149-158.
Henry, B. et al. (2001) μ- and δ -opioid receptor antagonist reduce levodopa-induced dyskinesia in the MPTP-lesioned primate model of Parkinson's disease. *Experimental Neurology* 171:139-146.
Herrero, M.T. et al. (1995) Effects of L-DOPA on preproenkephalin and preprotachykinin gene expression in MPTP-treated monkey striatum. *Neurosci.* 68:1189-1198.
Hill, M.P. et al. (2000) δ opioid receptor agonists as a therapeutic approach in Parkinson's disease. *Drugs News Perspect.* 13(5):261-268.
Hille, C.J. et al. (2001) Antiparkinsonian action of a δ opioid agonist in rodent and primate models of Parkinson's disease. *Exp. Neurol.* 172:189-198.
Jolkkonen, J. et al. 1995) L-DOPA reverses altered gene expression of substance P but not enkephalin in the caudate-putamen of common marmosets treated with MPTP. *Brain Res. Mol. Brain Res.* 32:297-307.
Maneuf, Y.P. et al. (1994) On the role of enkephalin cotransmission in the GABAergic striatal efferents to the globus pallidus. *Exp. Neurol.*125:65-71.
Negus, S.S. et al. (1994) Behavioral effects of the systemically active delta opioid agonist BW373U86 in rhesus monkeys. *J. Pharmacol. Exp. Ther.*, 270, 1025-34.

(Continued)

*Primary Examiner* — Shobha Kantamneni
(74) *Attorney, Agent, or Firm* — Marianne Fuierer; Moore & Van Allen, PLLC

(57) ABSTRACT

Compositions and methods for treatment of Parkinson's disease to reduce the negative side effects of the disease by administering a therapeutically effective diarylmethylpiperazine compound which exhibits delta opioid receptor agonist activity, and optionally, mu receptor antagonist activity.

1 Claim, 4 Drawing Sheets

(56) References Cited

OTHER PUBLICATIONS

Negus, S.S. et al. (1995) Role of delta opioid receptors in the reinforcing and discriminative stimulus effects of cocaine in rhesus monkeys. *J Pharmacol. Exp. Ther.*, 273: 1245-56.

Negus, S.S. et al. (1998) Behavioral effects of the delta-selective opioid agonist SNC80 and related compounds in rhesus monkeys. *J Pharmacol. Exp. Ther.*, 286: 362-75.

Nisbet, A.P. et al. (1995) Perproenkephalin and preprotachykinin messenger RNA expression in normal human basal ganglia and in Parkinson's disease. *Neurosci.* 66:361-376.

Silverdale, M.A. et al. (2003) Potential nondopaminergic drugs for Parkinson's disease. *Parkinson's Disease: Advances in Neurology* 91:273-291.

Figure 3A:
The effect of Formula (ii) dosed orally on locomotor activity of haloperidol-treated rats.
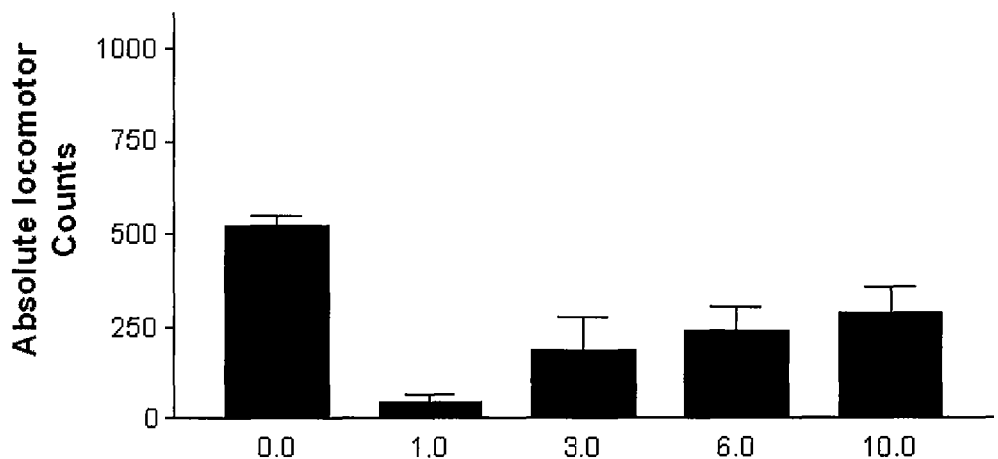
Figure 3B:
The effect of Formula (ii) dosed intraperitoneally on locomotor activity of haloperidol-treated rats.
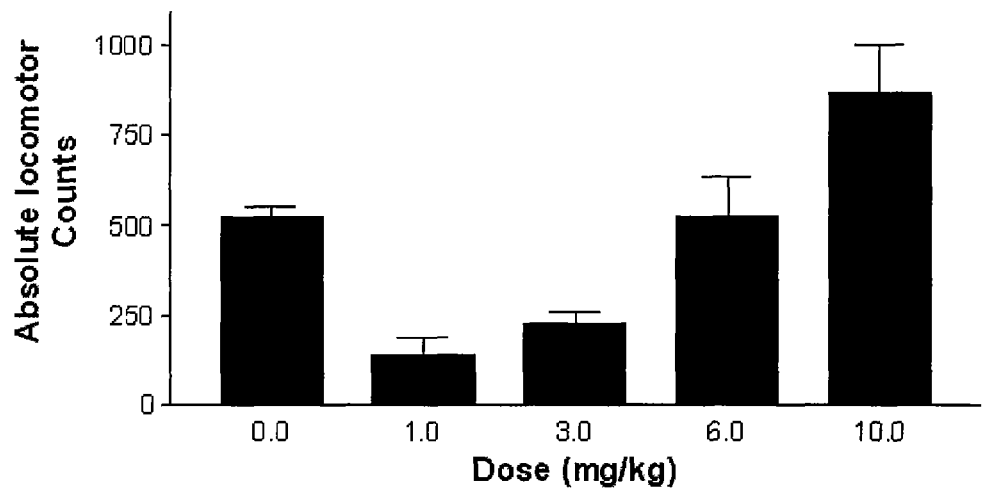
Figure 3

METHOD OF TREATING PARKINSON'S DISEASE WITH A DIARYLMETHYLPIPERAZINE COMPOUNDS EXHIBITING DELTA OPIOID RECEPTOR AGONIST ACTIVITY

CROSS REFERENCE TO RELATED APPLICATIONS

This application is a continuation of U.S. patent application Ser. No. 14/170,791 filed on Feb. 3, 2014 now U.S. Pat. No. 9,701,645, which in turn was a divisional application of and claiming priority to U.S. patent application Ser. No. 11/470,012, filed on Sep. 5, 2006, now U.S. Pat. No. 8,642,599, which in turn claimed priority to U.S. Provisional Application No. 60/714,187 filed on Sep. 2, 2005, the contents of which are incorporated by reference herein for all purposes.

BACKGROUND OF THE INVENTION

Field of the Invention

The present invention relates to compositions and methods of treatment for Parkinson's Disease, by administration to a subject suffering or susceptible to same, of a diarylmethylpiperazine compound that exhibits delta opioid receptor agonist and/or mu opioid receptor antagonist activity and optionally in combination with other active Parkinson treating agents.

Description of the Related Art

Parkinson's disease is a degenerative disorder identified by the loss of motor control progressing to loss of motor functions as well as Parkinsonian dementia in many cases. The pathophysiology of the disease is dominated by a loss of dopamine containing neurons in the brain, particularly in the basal ganglia areas.

Current medical therapy for Parkinson's disease is based primarily around the replacement of the dopamine deficit through the administration of L-DOPA with or without dopamine agonists. However, after 3-5 years of L-DOPA treatment alone patients develop motor fluctuations due to "wearing-off" of the therapeutic effect, "on-off" fluctuations in efficacy immediately after dosing, or most commonly, an "overshoot" of effect manifested as abnormal involuntary movements (AIMs; dyskinesias) (Hill et al., 2000; Silverdale et al., 2003). The co-administration of dopamine agonists (primarily ergot-derived) with L-DOPA slows the development of these side-effects but does not prevent their eventual onset (Hill et al., 2000; Silverdale et al., 2003). Critically, once patients have experienced L-DOPA-induced dyskinesias they are "primed" for dyskinesias in response to any currently available dopamine-based therapeutic (Hill et al., 2000). In light of these debilitating side-effects and the loss of efficacy over extended L-DOPA use, non-dopaminergic therapy for Parkinson's disease would be highly desirable, whether as a monotherapy or as an adjunct therapy to low-dose L-DOPA administration. One such target is the opioid receptor system, and the delta receptor subtype in particular (Hille et al, 2001).

While the role of the opioid peptides in the pathophysiology of Parkinson's disease is poorly understood compared to that of dopamine, the distribution of opioid peptides and receptor expression throughout the basal ganglia has prompted considerable investigation (Hille et al. 2001). The co-localization of met- and leu-enkephalin with GABA in striatal neurons projecting to the external globus pallidus (GPe) is well established (Cuello, et al. 1978; Gerfen, et al., 1988), while met-enkephalin has been shown to decrease depolarization-evoked GABA release from rat globus pallidus, an effect considered to be anti-parkinsonian in nature (Maneuf et al., 1994). In addition, met-enkephalin has been shown to be elevated in the striatum of parkinsonian rodent and primate models as well as in Parkinson's disease patients (Nisbet et al., 1995; Maneuf et al., 1994; De Ceballos et al., 1993). Furthermore, drug-induced dyskinesias in rodents, primates and Parkinson's disease patients have been shown to be associated with elevated levels of striatal preproenkephalin B (Nisbet et al., 1995; Herrero et al., 1995; Jolkkonen et al., 1995; Henry et al., 1996). With the identification of met-enkephalin as one of the primary endogenous ligand for the delta receptor, the anti-parkinson potential of delta receptor activation becomes clear.

Some anti-parkinsonian effect has been demonstrated for delta receptor activation by rodent and primate studies with the delta receptor-selective agonist, SNC80 (Hille et al, 2001). SNC80 is a highly selective delta receptor agonist and is an analogue of benzhydrylpiperazines such as BW373U86 (Chang et al., 1993). SNC80 at 10 mg/kg i.p. restored behavioral deficits observed in rats treated with reserpine or dopamine receptor antagonists (haloperidol or SCH23390) including ambulatory behavior, grooming, rearing, social interaction and exploration, and static investigation. When administered at similar dose levels to MPTP-treated marmosets, SNC80 restored motor activity, bradykinesia and disability scores to normal. The parkinsonian posture induced by MPTP treatment in this model was not statistically reversed by SNC80 although substantial improvements were observed in some individual animals (Hille et al., 2001).

These reports, in both rodent and non-human primate models of Parkinson's disease, indicate that the delta opioid receptor agonist SNC80 has a powerful anti-parkinsonian effect. Interestingly, even at relatively high doses behavior returned to normal levels but did not show the hyperkinesias associated with supra-optimal doses of L-DOPA (Hille et al, 2001). The mechanism of action appears to be via the delta receptor (Hille et al, 2001). However, SNC80 is neither orally active nor particularly safe for use in a clinical setting. SNC80 has been shown to produce seizure-like convulsions in mice and rats, and as such cannot be pursued for clinical study (Broom, et al., 2002).

A highly selective mu antagonist cyprodime was shown to reduce completely L-DOPA-induced dyskinesia in the MPTP-lesioned primate (marmosets) model of Parkinson's disease without attenuation of the anti-parkinsonian actions of L-DOPA (Henry et al., 2001). It appears that the highly selective mu antagonist cyprodime was more effective than less selective antagonists such as naltrexone and naltrindole at the dose of 10 mg/kg i.p. This data plus the demonstrated increase in the synthesis of proenkephalin A and B in basal ganglia in the animal model of L-DOPA-induced dyskinesia and in postmortem tissue from Parkinson's disease patients treated with conventional therapy (Nisbet et al., 1995; Maneuf et al., 1994; De Ceballos et al., 1993) provides strong evidence that mu-receptor activation may contribute to the development of dyskinesia in Parkinson's disease patients after chronic L-DOPA based therapy.

Thus, there is a need for an effective opioid-based treatment for Parkinson's disease that not only acts as a delta opioid receptor agonist but also optionally exhibits mu opioid receptor antagonist activity while negating the unwanted side effects of known opioid compositions currently used in the treatment of Parkinson's disease.

SUMMARY OF THE INVENTION

The present invention relates to a method of treating Parkinson's disease by administering a non-L-DOPA agent that avoids the dyskinetic side-effects produced by traditional treatments with L-DOPA and/or dopamine receptor agonists.

In another aspect, the present invention relates in one aspect to a method of treating Parkinson's disease in a subject, comprising administering to said subject an effective amount of a therapeutic composition comprising a compound that exhibits delta opioid receptor agonist, optionally in combination with other active Parkinson treating agents.

Preferably, the compound is a diarylmethylpiperazine compound that exhibits both delta opioid receptor agonist and optionally mu opioid receptor antagonist activity. The diarylmethylpiperazine compound may be administered in combination with other Parkinson's agents, including but not limited to, apomorphine, benztropine mesylate, entacapone, selegiline hydrochloride, parmipexole dihydrochloride, carbidopa, levodopa, pergolide, ropinirole hydrochloride, amantadine hydrochloride, tolcapone.

In another aspect, the present invention relates to a method of treating Parkinson's disease, comprising administering to said subject an effective amount of a therapeutic composition comprising a diarylmethylpiperazine compound of the general formula:

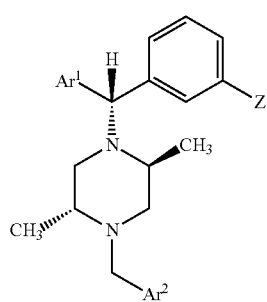

(1)

wherein:
Ar$^1$ is 6-member carbocyclic aromatic ring having on a carbon atom thereof a substituent Y, wherein Y is a carboxamide of the formula CONEt$_2$;
Z is selected from the group consisting of hydrogen, hydroxyl, and alkoxy; and
Ar$^2$ is a 6-member carbocyclic aromatic ring having on a carbon atom thereof a substituent X and wherein X is a halogen,
or a pharmaceutically acceptable ester or salt thereof; and wherein the diarylmethylpiperazine compound exhibits both delta opioid receptor agonist and mu opioid receptor antagonist activity.

Optionally, the method may include administering other Parkinson's treating agents of any suitable type, and may include, without limitation, apomorphine, benztropine mesylate, entacapone, selegiline hydrochloride, parmipexole dihydrochloride, carbidopa, levodopa, pergolide, ropinirole hydrochloride, amantadine hydrochloride, tolcapone.

Another aspect of the invention relates to a method of treating Parkinson's disease, the method comprising administering to said subject an effective amount of a therapeutic composition comprising at least one compound having a formula selected from the group consisting of:

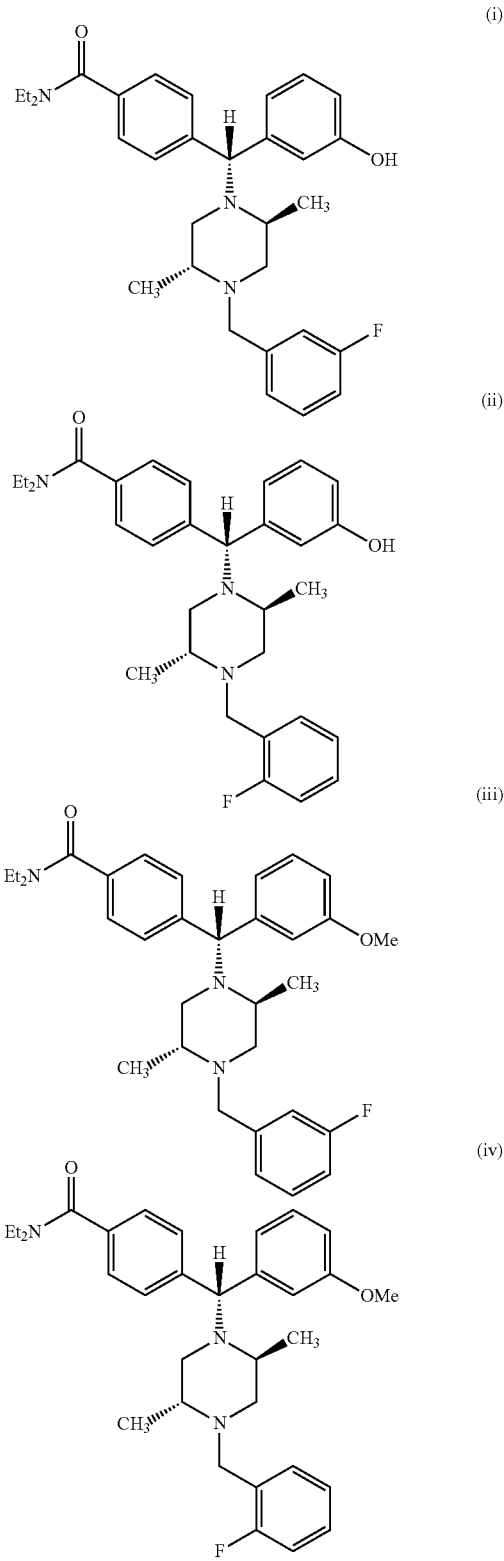

and pharmaceutically acceptable esters and salts of the foregoing compounds, and wherein the diarylmethylpiperazine compound exhibits delta opioid receptor agonist activity and optionally mu opioid receptor antagonist activity.

The therapeutic compositions may be administered by any suitable administrative mode, e.g., an administration modality selected from the group consisting of oral, rectal, topical, sub-lingual, mucosal, nasal, ophthalmic, subcutaneous, intramuscular, intravenous, transdermal, spinal, intrathecal, intracranial, intra-articular, intra-arterial, sub-arachnoid, bronchial, lymphatic, vaginal and intra-uterine administration.

A still further aspect of the present invention relates to a method of treating Parkinson's disease, comprising administering to said subject an effective amount of a therapeutic composition comprising at least one compound having a formula selected from the group consisting of:

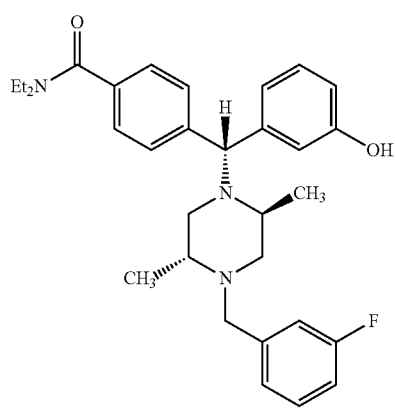

(i)

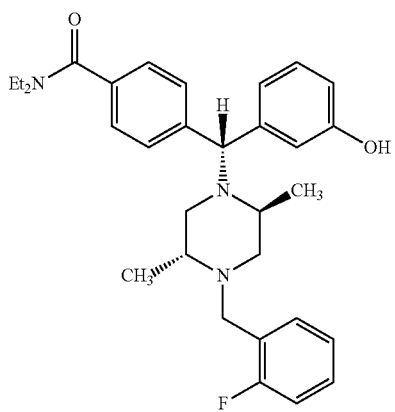

(ii)

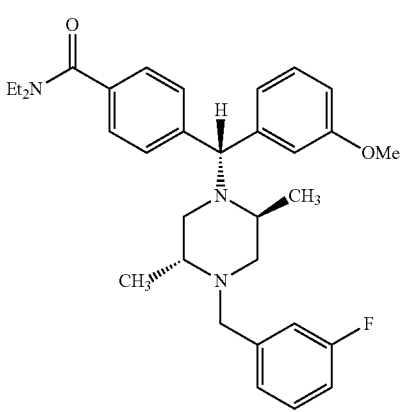

(iii)

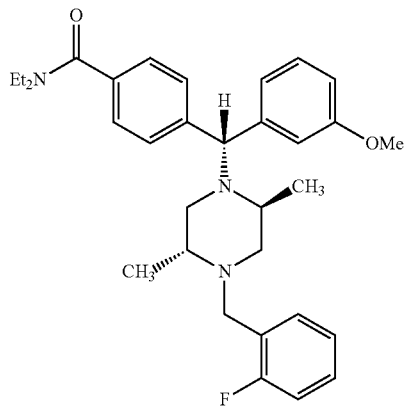

(iv)

and pharmaceutically acceptable esters and salts of the foregoing compounds; wherein the diarylmethylpiperazine compound exhibits delta opioid receptor agonist activity and optionally mu opioid receptor antagonist activity; in combination with another active Parkinson treating agent.

The active Parkinson treating agent may be of any suitable type, and may include, without limitation, apomorphine, benztropine mesylate, entacapone, selegiline hydrochloride, parmipexole dihydrochloride, carbidopa, levodopa, pergolide, ropinirole hydrochloride, amantadine hydrochloride, tolcapone.

In one specific embodiment according to the invention, wherein another active Parkinson treating agent is employed in the administered therapeutic composition, such other agent is not a diarylmethylpiperazine compound and/or a delta opioid receptor agonist.

An additional aspect of the invention relates to a composition for combating Parkinson's disease in a subject experiencing same comprising a diarylmethylpiperazine compound of the general formula:

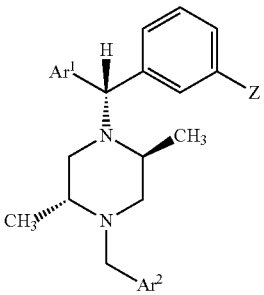

(1)

wherein:

$Ar^1$ is 6-member carbocyclic aromatic ring having on a carbon atom thereof a substituent Y, wherein Y is a carboxamide of the formula $CONEt_2$;

Z is selected from the group consisting of hydrogen, hydroxyl, and alkoxy; and

Are is a 6-member carbocyclic aromatic ring having on a carbon atom thereof a substituent X and wherein X is a halogen, or a pharmaceutically acceptable ester or salt thereof; and wherein the diarylmethylpiperazine compound exhibits delta opioid receptor agonist activity and optionally mu opioid receptor antagonist activity.

Another aspect of the present invention relates to a therapeutic composition for treatment of Parkinson's disease in a subject experiencing same, comprising a diarylmethylpiperazine compound of the formula selected from the group consisting of:

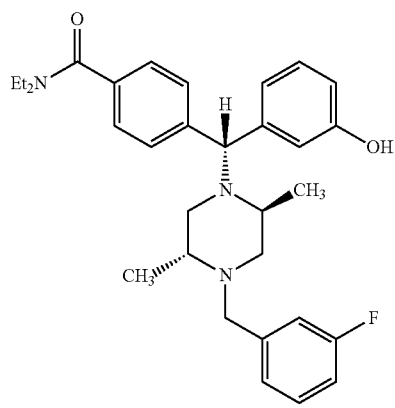
(i)

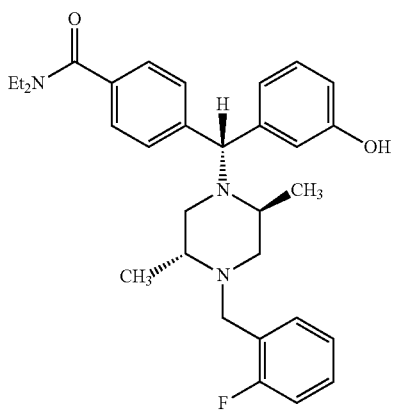
(ii)

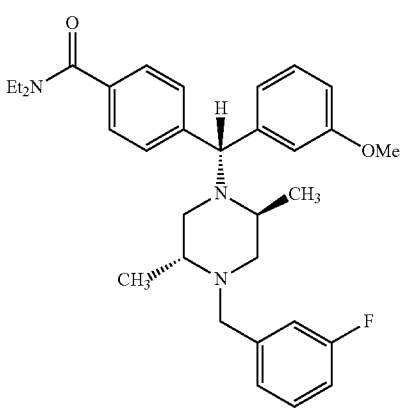
(iii)

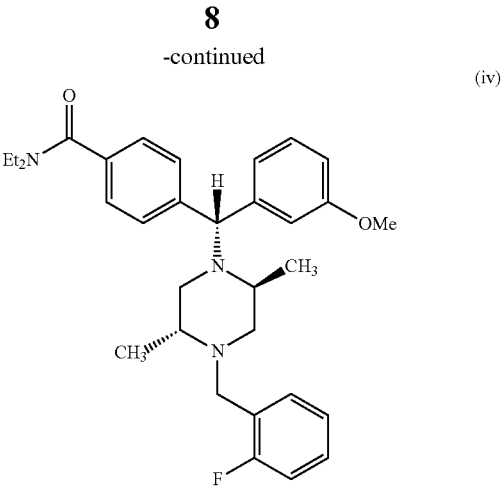
(iv)

and pharmaceutically acceptable esters and salts of the foregoing compound; wherein the diarylmethylpiperazine compound exhibits both delta agonist and mu antagonist activity.

Optionally, the composition may further comprise another Parkinson treating agent selected from the group consisting of apomorphine, benztropine mesylate, entacapone, selegiline hydrochloride, parmipexole dihydrochloride, carbidopa, levodopa, pergolide, ropinirole hydrochloride, amantadine hydrochloride, tolcapone.

Another aspect of the present invention relates to use of the compounds of the present invention, including Formula (i) or Formula (ii) or Formula (iii) or Formula (iv) in the manufacture of a medicament or pharmaceutical for the treatment of Parkinson's disease.

Another aspect of the present invention relates to a therapeutic composition for combating Parkinson's disease in a subject experiencing or susceptible to same, comprising a diarylmethylpiperazine compound of the general formula:

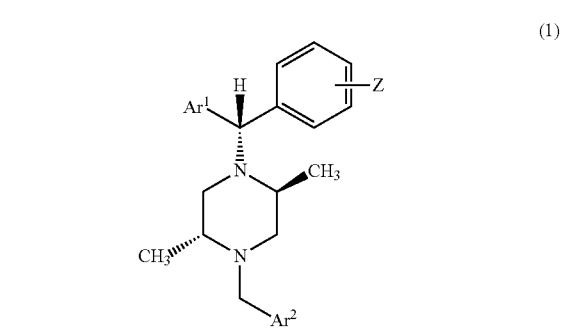
(1)

wherein:
Ar$^1$ is a 5- or 6-member carbocyclic or heterocyclic aromatic ring with atoms selected from the group consisting of carbon, nitrogen, oxygen and sulfur, and having on a first carbon atom thereof a substituent Y and on a second ring carbon thereof a substituent R$^1$,
Y is selected from the group consisting of:
hydrogen;
halogen;
$C_1$-$C_6$ alkyl, $C_2$-$C_6$ alkenyl, $C_2$-$C_6$ alkynyl;
$C_1$-$C_6$ haloalkyl;
$C_1$-$C_6$ alkoxy;
$C_3$-$C_6$ cycloalkoxy;

sulfides of the formula $SR^8$ where $R^8$ is $C_1$-$C_6$ alkyl, $C_2$-$C_6$ alkenyl, $C_2$-$C_6$ alkynyl, $C_3$-$C_6$ cycloalkyl, arylalkyl having a $C_5$-$C_{10}$ aryl moiety and a $C_1$-$C_6$ alkyl moiety, or $C_5$-$C_{10}$ aryl;

sulfoxides of the formula $SOR^8$ where $R^8$ is the same as above;

sulfones of the formula $SO_2R^8$ where $R^8$ is the same as above;

nitrile;

$C_1$-$C_6$ acyl;

alkoxycarbonylamino (carbamoyl) of the formula $NHCO_2R^8$ where $R^8$ is the same as above;

carboxylic acid, or an ester, amide, or salt thereof;

aminomethyl of the formula $CH_2NR^9R^{10}$ where $R^9$ and $R^{10}$ may be the same or different, and may be hydrogen, $C_1$-$C_6$ alkyl, $C_2$-$C_6$ alkenyl, $C_2$-$C_6$ alkynyl, $C_2$-$C_6$ hydroxyalkyl, $C_2$-$C_6$ methoxyalkyl, $C_3$-$C_6$ cycloalkyl, or $C_5$-$C_{10}$ aryl, or $R^9$ and $R^{10}$ together may form a ring of 5 or 6 atoms, the ring atoms selected from the group consisting of N and C; carboxamides of the formula $CONR^9R^{10}$ where $R^9$ and $R^{10}$ are the same as above, or $C_2$-$C_{30}$ peptide conjugates thereof; and sulfonamides of the formula $SO_2NR^9R^{10}$ where $R^9$ and $R^{10}$ are the same as above;

$R^1$ is hydrogen, halogen, or $C_1$-$C_4$ alkyl, $C_2$-$C_4$ alkenyl, $C_1$-$C_4$ alkynyl;

Z is selected from the group consisting of hydrogen, hydroxyl, halogen and alkoxy;

$Ar^2$ is a 5 or 6-member carbocyclic or heterocyclic aromatic ring with atoms selected from the group consisting of carbon, nitrogen, oxygen and sulfur, and having on a carbon atom thereof a substituent X X is selected from the group consisting of hydrogen, halogen (fluorine, bromine, chlorine, iodine), hydroxy and alkoxy;

or a pharmaceutically acceptable ester or salt thereof.

Various other aspects, features and embodiments of the invention will be more fully apparent from the ensuing disclosure and appended claims.

BRIEF DESCRIPTION OF THE FIGURES

FIG. 3 shows anti-parkinsonian syndrome effects of Formula (ii) after p.o. (oral; FIG. 3A) or i. p. (intraperitoneal; FIG. 3B) administration in haloperidol-treated rats.

DETAILED DESCRIPTION OF THE INVENTION

Figure 1:
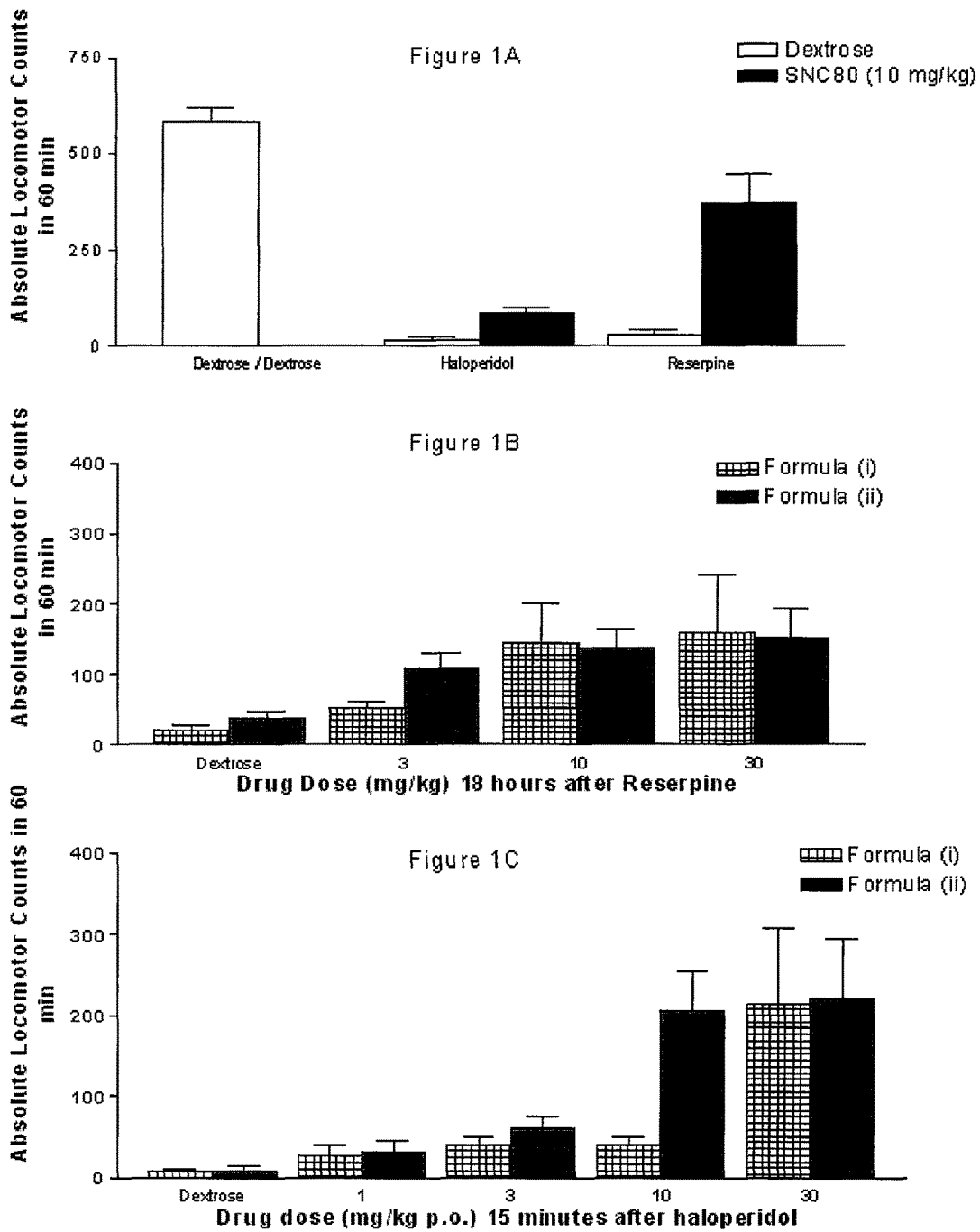
FIG. 1 shows the testing results of using compounds SNC80 (FIG. 1 A), Formulas (i) and (ii) (FIGS. 1B and C) in overcoming the negative effects of reserpine or haloperidol on locomotor activity.

In one broad method aspect of the present invention, a diarylmethylpiperazine compound that exhibits delta opioid receptor agonist activity and also preferably mu opioid receptor antagonist activity as hereinafter more fully described is administered to a subject in need of treatment for the treatment of Parkinson's disease.

The invention broadly contemplates the treatment of Parkinson's disease by using a mono-therapy treatment, involving compounds of the invention as singular therapeutic agents in administered therapeutic compositions, or co-therapy treatment, wherein a compound in accordance with the present invention is administered contemporaneously, e.g., simultaneously, or sequentially, with another therapeutic Parkinson agent.

In a particularly preferred method aspect of the invention, Parkinson's disease is treated by administering to a subject in need of such treatment an effective amount of a compound of formulae (i)-(iv) or a pharmaceutically acceptable ester or salt thereof.

Examples of pharmaceutically acceptable esters of compounds of formula (i) include carboxylic acid esters of the hydroxyl group in the compounds of formula (i) where Z=OH in which the non-carbonyl moiety of the carboxylic acid portion of the ester grouping is selected from straight or branched chain alkyl (e.g. n-propyl, t-butyl, n-butyl), alkoxyalkyl (e.g. methoxymethyl), arylalkyl (e.g. benzyl), aryloxyalky (e.g. phenoxymethyl), and aryl (e.g. phenyl); alkyl-, aryl-, or arylalkylsulfonyl (e.g. methanesulfonyl); amino acid esters (e.g. L-valyl or L-isoleucyl); dicarboxylic acid esters (e.g. hemisuccinate); carbonate esters (e.g. ethoxycarbonyl); carbamate esters (e.g. dimethylaminocarbonyl, (2-aminoethyl)aminocarbonyl); and inorganic esters (e.g. mono-, di- or triphosphate). However, esters that are not pharmaceutically acceptable may also find use, for example, in the preparation or purification of a pharmaceutically acceptable compound. All salts, whether or not derived from a pharmaceutically acceptable acidic moiety, are within the scope of the present invention.

Examples of pharmaceutically acceptable salts of the compounds of formula (i) include salts derived from an appropriate base, such as an alkali metal (for example, sodium, potassium), an alkaline earth metal (for example, calcium, magnesium), ammonium and $NR'_4{}^+$ (wherein R' is $C_1$-$C_4$ alkyl).

Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as $Na^+$, $NH_4{}^+$, or $NR'_4{}^+$ (wherein R' is for example a $C_{1-4}$ alkyl group).

For therapeutic use, salts of the compounds of formulae (i)-(iv) will be pharmaceutically acceptable, i.e., they will be salts derived from a pharmaceutically acceptable acid or base. However, salts of acids or bases that are not pharmaceutically acceptable may also find use, for example, in the preparation or purification of a pharmaceutically acceptable compound. All esters, whether or not derived from a pharmaceutically acceptable acid or base, are within the scope of the present invention.

In one particularly preferred aspect of the invention, the therapeutic treatment agent is a diarylmethylpiperazine compound of Formula (i)-(iv) or a pharmaceutically acceptable ester or salt thereof.

The compounds contemplated by the invention include those of the general formula, as well as physiologically functional derivatives thereof.

By "physiologically functional derivative" is meant a pharmaceutically acceptable salt, ether, ester or salt of an ether or ester of the compound of the general formula (i) or any other compound which, upon administration to the recipient, is capable of providing (directly or indirectly) the said compound of the general formula (i) or an active metabolite or residue thereof.

The present invention also contemplates pharmaceutical formulations, both for veterinary and for human medical use, which comprise as the active agent one or more compound(s) of the invention.

In such pharmaceutical formulations, the diarylmethylpiperazine compound preferably is utilized together with one or more pharmaceutically acceptable carrier(s) therefore and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, sub-lingual, mucosal, nasal, optic, ophthalmic, subcutaneous, intramuscular, intravenous, transdermal, spinal, intrathecal, intracranial, intra-articular, intra-arterial, sub-arachnoid, bronchial, lymphatic, vaginal and intra-uterine administration.

When the active agent of the present invention is utilized in a formulation comprising a liquid solution, the formulation advantageously may be administered parenterally. When the active Parkinson agent of the present invention is employed in a liquid suspension formulation or as a powder in a biocompatible carrier formulation, the formulation may be advantageously administered orally, rectally, or bronchially.

When the active Parkinson agent of the present invention is utilized directly in the form of a powdered solid, the active agent may advantageously be administered orally. Alternatively, it may be administered bronchially, via nebulization of the powder in a carrier gas, to form a gaseous dispersion of the powder that is inspired by the patient from a breathing circuit comprising a suitable nebulizer device.

In some applications, it may be advantageous to utilize the active Parkinson agent of the present invention in a "vectorized" form, such as by encapsulation of the active agent in a liposome or other encapsulant medium, or by fixation of the active Parkinson agent of the present invention, e.g., by covalent bonding, chelation, or associative coordination, on a suitable biomolecule, such as those selected from proteins, lipoproteins, glycoproteins, and polysaccharides.

The formulations comprising the active Parkinson agent of the present invention may conveniently be presented in unit dosage forms and may be prepared by any of the methods well known in the art of pharmacy. Such methods generally include the step of bringing the active Parkinson compound(s) of the present invention into association with a carrier that constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active Parkinson agent of the present invention to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the active Parkinson agent of the present invention with preservative agents and isotonic agents. Such formulations are preferably adjusted to a pH and isotonic state compatible with the nasal mucous membranes.

Formulations for rectal or vaginal administration may be presented as a suppository or pessary with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active Parkinson agent of the present invention dissolved or suspended in one or more media, such as mineral oil, petroleum, polyhydroxy alcohols, or other bases used for topical pharmaceutical formulations.

Transdermal formulations may be prepared by incorporating the active Parkinson agent of the present invention in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

Depending on the specific condition to be treated, animal subjects may be administered compounds of the present invention at any suitable therapeutically effective and safe dosage, as may readily be determined within the skill of the art, and without undue experimentation.

In general, while the effective dosage of compounds of the invention for therapeutic use may be widely varied in the broad practice of the invention, depending on the specific condition involved, as readily determinable within the skill of the art, suitable therapeutic doses of the compounds of the invention, for each of the appertaining compositions described herein, and for achievement of therapeutic benefit in treatment of each of the conditions described herein, will be in the range of 10 micrograms (m) to 100 milligrams (mg) per kilogram body weight of the recipient per day, preferably in the range of 50 μg to 75 mg per kilogram body weight per day, and most preferably in the range of 100 μg to 50 mg per kilogram body weight per day. The desired dose may be presented as two, three, four, five, six, or more sub-doses administered at appropriate intervals throughout the day. These sub-doses may be administered in unit dosage forms, for example, containing from 10 μg to 1000 mg, preferably from 50 μg to 500 mg, more preferably from 50 μg to 250 mg, and most preferably from 50 μg to 10 mg of active ingredient per unit dosage form.

The mode of administration and dosage forms will of course affect the therapeutic amounts of the Parkinson agent of the present invention which are desirable and efficacious for the given treatment application.

For example, orally administered dosages typically are at least twice, e.g., 2-10 times, the dosage levels used in parenteral administration methods, for the same active ingredient. In oral administration, dosage levels for compounds of the present invention may be on the order of 5-200 mg/70 kg body weight/day. In tablet dosage forms, typical active agent dose levels are on the order of 10-100 mg per tablet.

The following examples are illustrative of synthetic procedures that may be advantageously utilized to synthesize compounds of the present invention.

Example 1 (Formula (i)

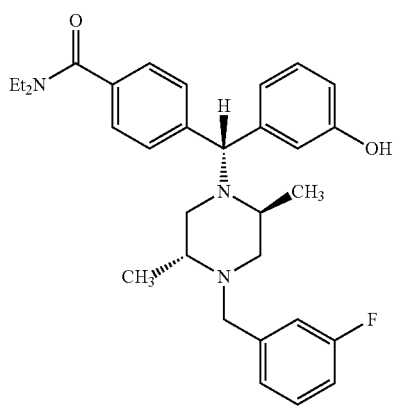

4-((alpha-R)-alpha-((2S,5R)-2,5-Dimethyl-4-(3-fluorobenzyl)-1-piperazinyl)-3-hydroxybenzyl)-N,N-diethylbenzamide Method A—Alkylation with Phenol Protection A solution of 3-bromophenol (400 g, 2.31 mol), tert-butylchlorodimethylsilane (391 g, 2.54 mol), and imidazole (346 g, 5.08 mol) in 5000 mL of dichloromethane was stirred overnight at room temperature. The reaction solution was poured into water (2000 mL) and the layers separated. The organic layer was washed with 1N aqueous sodium hydroxide solution (3×1500 mL) and water (2×1500 mL) before passing through a pad of silica gel (400 g, silica 60, 230-400 mesh). The silica gel was washed with dichloromethane (2×500 mL), the filtrates combined and the solvent removed under reduced pressure to give 3-(bromophenoxy)-tert-butyldimethylsilane (669 g, 98.4%) as a clear pale yellow liquid. NMR (300 MHz, CDCl$_3$): δ 0.2 (s, 6H); 1.0 (s, 9H); 6.75 (m, 1H); 7.0 (br s, 1H); 7.1 (m, 2H).

3-tert-Butyldimethylsilyloxyphenylmagnesium bromide was formed by the slow addition of a mixture of 3-bromophenoxy-tert-butyldimethylsilane (27.3 g, 92.6 mmol) and dibromoethane (3.45 g, 18.4 mmol) in inhibitor-free anhydrous tetrahydrofuran (100 mL) to a solution of magnesium turnings (3.57 g, 147 mmol) in inhibitor-free anhydrous tetrahydrofuran (200 mL) at reflux. After stirring for one hour at reflux the light brown clear mixture was cooled to room temperature.

4-Carboxybenzaldehyde (100.3 g, 0.67 mol) was dissolved/suspended in toluene (1200 mL), dimethylformamide (0.15 mL) was added and the suspension was stirred during the dropwise addition of thionyl chloride (53.5 mL, 87.2 g, 0.73 mol). The reaction mixture was heated to reflux under nitrogen and stirred for 2 h, during which time much, but not all of the aldehydo-acid passed into solution. A further quantity of thionyl chloride (20 mL, 32.6 g, 0.27 mol) was added and reflux continued overnight. The clear reaction mixture was evaporated, and the residue dissolved in anhydrous tetrahydrofuran (1500 mL). The solution was cooled in an ice/water bath and diethylamine (173 mL, 122 g, 1.67 mol (2.5 equivalents)) was added dropwise to the stirred solution. The ice-bath was removed and stirring continued for 2.5 h. The reaction mixture was filtered to remove the white crystalline diethylamine hydrochloride by-product. The crystals were washed with ethyl acetate (2×600 mL), and the washings set aside. The tetrahydrofuran filtrate was evaporated, and the residue dissolved in the ethyl acetate washings. The solution was washed sequentially with 1 M-hydrochloric acid (2×600 mL), water (2×300 mL), dilute sodium carbonate solution (saturated Na$_2$CO$_3$: H$_2$O, 1:1, 2×600 mL), water (2×300 mL) and saturated sodium chloride solution (300 mL). The organic layer was separated, dried over anhydrous sodium sulfate and evaporated to yield 4-formyl-N,N-diethylbenzamide as a pale brown oil (115.7 g, 84%) which was used without further purification.

In a 1000 mL round bottom flask fitted with a condenser and Dean-Stark trap were combined 4-formyl-N,N-diethylbenzamide (9.50 g, 46.3 mmol), benzotriazole (5.51 g, 46.3 mmol), and (2R,5S)-1-allyl-2,5-dimethylpiperazine (7.15 g, 46.3 mmol, Chirotech Division of Dowpharma, The Dow Chemical Company, Cambridge, England) with toluene (400 mL). The reaction mixture was heated to reflux under nitrogen until no additional water was observed in the trap (ca. 2 hours). The reaction mixture was cooled to room temperature and concentrated under vacuum to leave a volume of approximately 50 mL. Anhydrous tetrahydrofuran (100 mL) was added to the flask under nitrogen with stirring to dissolve all residue. The solution of benzotriazole adduct was added to the solution of 3-tert-butyldimethylsilyloxyphenylmagnesium bromide (above) at room temperature via double-ended needle. After stirring for 2 hours, the reaction was quenched by addition of saturated aqueous ammonium chloride (20 mL). Anhydrous magnesium sulfate (20 g) was added and the reaction was filtered. Solvent was removed under vacuum and the residue was redissolved in ethyl acetate (800 mL). The ethyl acetate solution was washed with 1 M sodium hydroxide (4×200 mL), water (200 mL), and saturated aqueous sodium chloride (200 mL). The organic layer was dried over anhydrous magnesium sulfate and the solvent removed to give a dark oil. The oil was dissolved in tetrahydrofuran (250 mL) and 3 M hydrochloric acid (350 mL) and stirred for 2 hours at room temperature. The reaction solution was extracted with a mixture of diethyl ether/ethyl acetate (2:1, 3×250 mL). Ethyl acetate (300 mL) was added to the aqueous layer and pH was adjusted to 8 with aqueous sodium hydroxide. Layers were separated and the aqueous portion was extracted with another ethyl acetate (3×300 mL). The combined organic extracts were washed with saturated aqueous sodium chloride, dried over anhydrous sodium sulfate, and the solvent removed under vacuum to give a brown residue (12.4 g). The residue was purified by chromatography on silica gel (300 g), eluting with a gradient of ethanol in dichloromethane (1-15%), to give 4-((alpha-R)-alpha-((2S,5R)-4-allyl-2,5-dimethyl-1-piperazinyl)-3-hydroxybenzyl)-N,N-diethylbenzamide as a colorless gum (5.54 g, 27% from 4-formyl-N,N-diethylbenzamide).

4-((alpha-R)-alpha-((2S,5R)-4-Allyl-2,5-dimethyl-1-piperazinyl)-3-hydroxybenzyl)-N,N-diethylbenzamide (4.87 g, 11.2 mmol) was dissolved in methylene chloride (60 mL) and triethylamine (5.15 mL, 3.73 g, 37 mmol) added. N-Phenyl bis(trifluoromethanesulfonimide) (4.40 g, 12.3 mmol) was added and the reaction mixture sealed under nitrogen and stirred at room temperature overnight. The reaction mixture was evaporated to dryness, the residue dissolved in ethyl acetate (100 mL), and the solution extracted with aqueous sodium carbonate solution (5%, 2×75 mL). The organic layer was separated, dried over anhydrous sodium sulfate and evaporated to yield a viscous amber oil. The residue was dissolved in methylene chloride (30 mL), applied to a column of silica gel (1000 g), and eluted with ethanol/methylene chloride (2:98 v/v). Pure fractions containing desired product, as evidenced by t.l.c. (silica gel, EM60F$_{254}$, 2% NH$_4$OH in ethyl acetate, R$_f$=0.78) were evaporated to dryness to yield 4-((alpha-R)-alpha-((2S,5R)-4-Allyl-2,5-dimethyl-1-piperazinyl)-3-trifluoromethyl-sulfonyloxybenzyl)-N,N-diethylbenzamide (4.03 g) as a yellow/amber oil. $^1$H NMR (CDCl$_3$, 500 MHz); δ 1.00 (d, J=6.2 Hz, 3H); 1.12 (br m, 3H); 1.21 (d, J=6.1 Hz, 3H); 1.25 (br m, 3H); 1.83 (t, J=10.6 Hz, 1H); 2.60 (m, 3H); 2.91 (dd J=11.4, 2.7, 1H); 3.02 (m, 1H); 3.18 (br s, 2H); 3.28 (br m, 2H); 3.46 (dd, J=13.7, 5.5 Hz, 1H); 3.55 (br m, 2H); 5.25 (m, 2H); 5.31 (s, 1H); 5.88 (m, 1H); 7.02 (d, J=7.7 Hz, 1H); 7.05 (s, 1H); 7.23 (m, 2H); 7.32 (d, J=8.1 Hz, 2H); 7.40 (d, J=8.1 Hz, 2H); 7.46 (t, J=7.9 Hz, 1H).

A solution of 4-((alpha-R)-alpha-((2S,5R)-4-allyl-2,5-dimethyl-1-piperazinyl)-3-trifluoromethylsulfonyloxybenzyl)-N,N-diethylbenzamide (4.03 g, 7.20 mmol) and thiosalicylic acid (1.32 g, 8.52 mmol) in anhydrous tetrahydrofuran (25 mL) was stirred under nitrogen for 3 h at room temperature with a catalyst solution prepared by dissolution of bis(dibenzylidineacetone)palladium (204 mg, 0.355 mmol) and 1,4-bis(diphenylphosphino)butane (151 mg, 0.355 mmol) in tetrahydrofuran (3 mL). The reaction mixture was evaporated to dryness, the residue dissolved in a mixture of ethyl acetate/ether (1:3, 125 mL) and extracted with aqueous sodium carbonate solution (5%, 2×75 mL). The organic layer was diluted with two volumes of pentane and extracted with 3M-hydrochloric acid (5×25 mL). The aqueous solution was adjusted to pH 9-10 with concentrated ammonia solution and extracted with methylene chloride (3×50 mL). The combined organic extracts were dried over anhydrous sodium sulfate and evaporated to yield 4-((alpha-R)-alpha-((2S,5R)-2,5-dimethyl-1-piperazinyl)-3-trifluoromethyl-sulfonyloxybenzyl)-N,N-diethylbenzamide as a brittle pale yellow foam (3.53 g). The product showed a single spot on thin layer chromatography (silica gel, EM60F$_{264}$, 2% NH$_4$OH in ethyl acetate, R$_f$=0.33). $^1$H NMR (CDCl$_3$, 500 MHz); δ 0.95 (d, J=6 Hz, 3H); 1.13 (br m, 3H); 1.20 (d, J=6.1 Hz, 3H); 1.26 (br m, 3H); 1.50 (t, J=9.7 Hz, 1H); 2.31 (m, 1H); 2.64 (dd J=11.3, 2.5, 1H); 2.71 (m, 1H); 2.95 (m, 1H); 3.29 (br m, 2H); 3.56 (br m, 2H); 5.43 (s, 1H); 7.04 (m, 1H); 7.21 (d, J=7.7, 1H); 7.24 (dd, J=8.2, 2.2 Hz, 1H); 7.34 (d, J=8.2 Hz, 2H); 7.42 (d, J=8.1 Hz, 2H); 7.48 (t, J=8 Hz, 1H).

A solution of 4-((alpha-R)-alpha-((2S,5R)-2,5-dimethyl-1-piperazinyl)-3-trifluoromethyl-sulfonyloxybenzyl)-N,N-diethylbenzamide (3.522 g, 6.0 mmol) and sodium iodide (90 mg, 0.6 mmol) in acetonitrile (30 mL) was stirred during the addition of triethylamine (3.0 mL, 2.186 g, 21.6 mmol) followed by 3-fluorobenzyl bromide (1.472 mL, 2.268 g, 12.0 mmol). An immediate turbidity was observed, thickening to a white crystalline precipitate as the reaction progressed. The reaction mixture was sealed under nitrogen and stirred at room temperature. After 18 h the solvent was removed by evaporation under reduced pressure and the residue partitioned between ethyl acetate (30 mL) and saturated sodium bicarbonate solution (10 mL). The organic layer was separated and the aqueous portion further extracted with ethyl acetate (3×15 mL). The combined organic extract and washings were dried over sodium sulfate, the solution evaporated to dryness and re-dissolved in ethyl acetate (~5 mL). The solution was applied to an intermediate (4×15 cm) Biotage column and eluted with ethyl acetate, collecting fractions of 20 mL. Fractions containing pure material as evidenced by thin layer chromatography (silica, EM60F$_{254}$, developed with ethyl acetate, R$_f$ 0.9) were pooled and evaporated to yield a yellow/orange oil (3.01 g). The oil was dissolved in ethanol (30 mL) and aqueous sodium hydroxide solution (10.0 mL, 2.5-M, 25 mmol) was added. The initially cloudy suspension clarified to a yellow solution that was set aside at room temperature for 3 h. The mixture was evaporated under reduced pressure to remove ethanol, and evaporation continued until condensation of water indicated complete removal of ethanol. The cloudy suspension of the oily sodium salt of the phenol was diluted to 20 mL with water to yield a clear yellow solution. The pH of the strongly basic solution was adjusted to 8.5-9 by passage of carbon dioxide gas (from dry ice) to yield a dense white flocculent precipitate. The solid was removed by filtration and washed thoroughly with cold water, including twice re-slurrying of the precipitate on the sinter with fresh water. The solid was air-dried on the sinter overnight, then dried under vacuum at 1 mm Hg at room temperature to yield 4-((alpha-R)-alpha-((2S,5R)-2,5-dimethyl-4-(3-fluorobenzyl)-1-piperazinyl)-3-hydroxybenzyl)-N,N-diethylbenzamide as a white solid (2.062 g, 67%) Calc. for C$_{31}$H$_{38}$FN$_3$O$_2$ 0.5 H$_2$O: C, 72.63; H, 7.67; N, 8.20; F, 3.71. Found C, 72.77; H, 7.52; N, 8.18; F, 3.61%. $^1$H NMR (CDCl3, 300 MHz); δ 1.05 (d, J=5.9 Hz, 6H); 1.11 (br m, 3H); 1.23 (br m, 3H); 2.00 (m, 2H); 2.59 (br m, 2H); 2.62 (d, J=11.4 Hz, 1H); 2.68 (d, J=11.0 Hz, 1H); 3.19 (d, J=13.6 Hz, 1H); 3.28 (br m, 2H); 3.54 (br m, 2H); 3.89 (d, J=13.9 Hz, 1H); 5.01 (s, 1H); 6.15 (v br s, 1H); 6.63 (s, 1H); 6.70 (m, 2H); 6.91 (t, J=8.8 Hz, 1H); 7.07 (m, 2H); 7.14 (t, J=7.8 Hz, 1H); 7.22 (m, 1H); 7.28 (d, J=8.2 Hz, 2H); 7.44 (d, J=8.1 Hz, 2H).

Method B—Reductive Alkylation

A solution of 4-[(R)-((2S,5R)-4-allyl-2,5-dimethyl-1-piperazinyl)-(3-hydroxyphenyl)-methyl]-N,N-diethylbenzamide (10.89 g, 25 mmol, from Method A) and thiosalicylic acid (4.63 g, 30 mmol) in anhydrous tetrahydrofuran (50 mL) was stirred with a catalyst solution prepared by dissolution of bis(dibenzylidineacetone)palladium (0.718 g, 1.25 mmol) and 1,4-bis(diphenylphosphino)butane (0.533 g, 1.25 mmol) in tetrahydrofuran (10 mL) at room temperature under nitrogen for 1.5 hours (J. P. Genet, S. Lemaire-Audoire, M. Savignac, *Tetrahedron Letters*, 36, 1267-1270 (1995)). The reaction mixture was concentrated under reduced pressure and the residue was partitioned between ethyl acetate (150 mL) and aqueous sodium carbonate solution. The layers were separated and diethyl ether (250 mL) was added to the organic layer. This was extracted with 5% sodium carbonate solution (2×150 mL). The organic layer was diluted with pentane (500 mL) and extracted with 3 M hydrochloric acid (6×30 mL). The aqueous solution was adjusted to pH 9-10 with saturated aqueous sodium carbonate solution and extracted with methylene chloride (3×100 mL). The combined organic extracts were dried over anhydrous sodium sulfate and the solvent was removed under reduced pressure to yield 4-[(R)-((2S,5R)-2,5-dimethyl-1-piperazinyl)-(3-hydroxyphenyl)methyl]-N,N-diethylbenzamide as a brittle pale yellow foam (10.24 g). The product showed a single peak on HPLC (Zorbax C-8, isocratic 40% 0.01 M $NH_4OAc$ in MeOH, 3 min; linear gradient to 100% MeOH, 45 min; isocratic MeOH, 5 min; 1.0 mL/min; $\delta_{obs}$=210 nm, Rt=19.24 min). Calc. for $C_{24}H_{33}N_3O_2$ 0.1 EtOAc 0.4 $CH_2Cl_2$: % C, 67.96; H, 7.96; N, 9.59. Found: % C, 67.90; H, 8.03; N, 9.54. $^1H$ NMR ($CDCl_3$, 300 MHz): δ 7.42 (d, J=8.1 Hz, 2H); 7.26 (d, J=8.3 Hz, 2H); 7.11 (t, J=7.8 Hz, 1H); 6.72 (d, J=8.1 Hz, 1H); 6.65 (s, 1H); 6.59 (d, J=7.6 Hz, 1H); 5.16 (s, 1H); 4.93 (v br s, 2H); 3.51 (br m, 2H); 3.27 (br m, 2H); 3.02-2.97 (m, 1H); 2.92 (d, J=10.5 Hz, 1H); 2.66 (br d, J=8.5 Hz, 1H); 2.60-2.45 (m, 1H); 1.84 (dd, J=11.3, 8.3 Hz, 1H); 1.27-1.15 (m, 3H); 1.10 (d, J=6.1 Hz, 3H overlapping with m, 3H); 1.02 (d, J=6.1 Hz, 3H).

Glacial acetic acid (0.635 mL, 11.1 mmol) was added to a solution of 4-[(R)-((2S,5R)-2,5-dimethyl-1-piperazinyl)-(3-hydroxyphenyl)methyl]-N,N-diethylbenzamide (1.98 g, 5 mmol) and 3-fluorobenzaldehyde (1.24 g, 10 mmol) in anhydrous tetrahydrofuran (35 mL). While stirring briskly, sodium triacetoxyborohydride (2.12 g, 10 mmol) was added in 50-100 mg portions, allowing effervescence to subside after each addition. The reaction was monitored for absence of starting material by HPLC. After stirring at room temperature for 16 hours, additional 3-fluorobenzaldehyde (0.62 g, 5 mmol), acetic acid (0.318 mL, 5 mmol), and sodium triacetoxyborohydride (1.06 g, 5 mmol) were added. After stirring an additional 4 hours, the reaction mixture was concentrated under reduced pressure and the residue was partitioned between ethyl acetate (50 mL) and 3 M hydrochloric acid (25 mL). The layers were separated and the organic layer was extracted again with 3 M hydrochloric acid (25 mL). The aqueous solution was adjusted to pH 9-10 with 5 M sodium hydroxide solution, resulting in the formation of chunky white precipitate. Brief sonication followed by continuous stirring for 60 hours allowed hydrolysis of any residual ethyl acetate, as well as complete precipitation of product. The white solid was filtered, washed with cold water, and further dried under reduced pressure to yield 4-[(R)-((2S,5R)-2,5-dimethyl-4-(3-fluorobenzyl)-1-piperazinyl)(3-hydroxyphenyl)-methyl]-N,N-diethylbenzamide (1.78 g, 82.3% yield from 4-[(R)-((2S,5R)-4-allyl-2,5-dimethyl-1-piperazinyl)-(3-hydroxyphenyl)-methyl]-N,N-diethyl-benzamide). The product showed a single peak on HPLC (Zorbax C-8, isocratic 40% 0.01 M $NH_4OAc$ in MeOH, 3 min; linear gradient to 100% MeOH, 45 min; isocratic MeOH, 25 min; 1.0 mL/min; $\delta_{obs}$=210 nm, Rt=43.51 min). Calc. for $C_{31}H_{38}FN_3O_2$ 0.5 $H_2O$: % C, 72.63; H, 7.67; N, 8.20; F, 3.71. Found: % C, 72.77; H, 7.52; N, 8.18; F, 3.61.

Method C—Direct Alkylation

To 4-[(R)-((2S,5R)-2,5-dimethyl-1-piperazinyl)-(3-hydroxyphenyl) methyl]-N,N-diethyl-benzamide (0.79 g, 2 mmol) and sodium iodide (30 mg, 0.2 mmol) in acetonitrile (10 mL) was added triethylamine (1.0 mL, 7.2 mmol), followed by 3-fluorobenzylbromide (0.76 g, 4 mmol). The reaction mixture was sealed under nitrogen and stirred at ambient temperature for 20 hours. The reaction mixture was concentrated under reduced pressure and the residue was partitioned between ethyl acetate (150 mL) and saturated sodium carbonate solution (15 mL) diluted with water (50 mL). The organic layer was separated and the aqueous layer was extracted with ethyl acetate (3×75 mL). The combined organic extracts were dried over anhydrous sodium sulfate and magnesium sulfate. The solvent was removed under reduced pressure to yield a light yellow solid (0.90 g). This solid was dissolved in isopropanol (30 mL) upon heating to boiling, and water (20 mL) was added slowly while swirling and keeping the solution hot. Crystallization occurs as solution begins to cool. Crystallization was allowed to proceed overnight. Crystals were collected and washed sparingly with isopropanol: water/1:1. Drying under 5 mm Hg at 40° C. for 48 hours yielded 4-[(R)-((2 S,5R)-2,5-dimethyl-4-(3-fluorobenzyl)-1-piperazinyl)(3-hydroxyphenyl)methyl]-N,N-diethyl-benzamide as old ivory colored crystals (0.77 g, 76.4% from 4-[(R)-((2S,5R)-4-allyl-2,5-dimethyl-1-piperazinyl)-(3-hydroxyphenyl)-methyl]-N,N-diethylbenzamide). Calc. for $C_{31}H_{38}FN_3O_2$.0.25 $H_2$ O.0.1 $^iPrOH$: % C, 73.12; H, 7.70; N, 8.17; F, 3.69. Found: % C, 73.13; H, 7.73; N, 8.24; F, 3.53.

Method D—Assembly from (2R,5S)-1-(3-fluorobenzyl)-2,5-dimethylpiperazine

In a 3 L round bottom flask fitted with a condenser and Dean-Stark trap are combined 4-formyl-N, N-diethylbenzamide (20.53 g, 100 mmol), benzotriazole (11.91 g, 100 mmol), and (2R,5S)-1-(3-flourobenzyl)-2,5-dimethylpiperazine (22.23 g, 100 mmol, Chirotech Division of Dowpharma, The Dow Chemical Company, Cambridge, England) with 1000 mL of toluene. The reaction is heated to reflux under nitrogen until no additional water is observed in the trap (ca. 3 hours). The reaction is cooled to room temperature and concentrated under vacuum to leave a volume of approximately 300 mL. Anhydrous tetrahydrofuran (500 mL) is added to the benzotriazole adduct under nitrogen with stirring until dissolved. To this solution is added the solution of 3-tert-butyldimethylsilyloxyphenylmagnesium bromide (from Method A) at room temperature via double-ended needle. After stirring for approximately 2 hours, the reaction is quenched by the addition of saturated aqueous ammonium chloride solution (50 mL) and stirred for 15 minutes. Anhydrous magnesium sulfate (50 g) is added, stirred for approximately 1 hour, and the reaction is filtered. The solvent is removed under reduced pressure and the residue is dissolved in ethyl acetate (1000 mL). The ethyl acetate solution is washed with 1 M sodium hydroxide (5×400 mL), water (4×400 mL), and saturated aqueous sodium chloride solution (400 mL). The organic layer is dried over anhydrous magnesium sulfate and the solvent is removed to give a viscous oil. The oil is dissolved in 500 mL of tetrahydrofuran and 300 mL of 3 M hydrochloric acid and stirred for approximately 1.5 hours at room temperature. Upon completion of the desilylation, the reaction is diluted with water (300 mL) and concentrated under vacuum to about half the original volume. This solution is extracted with pentane (2×500 mL). The aqueous layer is adjusted to pH 8-9 with 5 M sodium hydroxide and extracted with ethyl acetate (250 mL). The layers are separated and the aqueous portion is extracted with more ethyl acetate (250 mL). The combined organic extracts are washed with saturated aqueous sodium chloride solution, dried over anhydrous sodium sulfate, and the solvent is removed under reduced pressure to give a viscous oil. This residue is dissolved in ethyl acetate (25 mL), seeded with crystals of the authentic compound, and allowed to crystallize overnight (seed crystals can be obtained from hot 2-propanol with addition of water). The crystals are filtered and washed sparingly with cold ethyl acetate. Drying under 5 mm Hg at room temperature yields the desired product 4-[(R)-((2S,5R)-4-(3-fluorobenzyl)-2,5-dimethyl-1-piperazinyl)-(3-hydroxy-phenyl)-methyl]-N,N-diethylbenzamide as tan to off-white crystals, free from the undesired epimer. This solid is dissolved in isopropanol (300 mL) upon heating to boiling, and water (200 mL) is added slowly while swirling and keeping the solution hot. Crystallization occurs as solution begins to cool and is allowed to proceed overnight. Crystals are collected and washed sparingly with cold isopropanol:water/ 1:1. Drying under 5 mm Hg at 40° C. for 48 hours yields 4-[(R)-((2S,5R)-2,5-dimethyl-4-(3-fluorobenzyl)-1-piperazinyl)(3-hydroxyphenyl)methyl]-N,N-diethyl-benzamide as ivory colored crystals (expected yield ~30% from 4-formyl-N,N-diethylbenzamide).

Example 2 (Formula (ii))

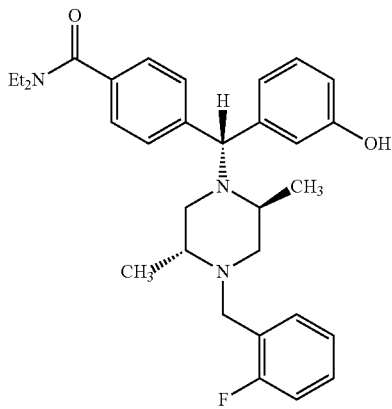

4-((Alpha-R)-Alpha-((2S,5R)-2,5-Dimethyl-4-(2-fluorobenzyl)-1-piperazinyl)-3-hydroxybenzyl)-N,N-diethylbenzamide 4-((alpha-R)-alpha-((2S,5R)-2,5-Dimethyl-1-piperazinyl)-3-trifluoromethylsulfonyloxy-benzyl)-N,N-diethylbenzamide (from Example 1, Method A, 527.6 mg, 1.0 mmol) was dissolved in acetonitrile (4.0 mL) and sodium iodide (15 mg, 0.1 mmol) added. The suspension was stirred during the addition of triethylamine (500 µL (363 mg), 3.59 mmol), followed by 2-fluorobenzyl bromide (241 µL (378 mg), 2.0 mmol). The reaction mixture was sealed under nitrogen and stirred overnight at room temperature. The reaction mixture was evaporated to dryness and partitioned between ethyl acetate (10 mL) and saturated aqueous sodium bicarbonate solution (2.5 mL). The supernatant organic layer was removed, and the aqueous portion washed with ethyl acetate (3×10 mL). The combined organic extract and washings were dried over anhydrous sodium sulfate and evaporated to a golden oil. The residue was dissolved in ethyl acetate (7 mL), applied to a pre-packed intermediate (4×15 cm, Biotage) column and eluted with ethyl acetate. Pure fractions containing desired product, as evidenced by t.l.c. (silica gel, EM60F$_{264}$, 100% ethyl acetate, R$_f$=0.77) were evaporated to dryness to yield the intermediate 4-((alpha-R)-alpha-((2S,5R)-2,5-Dimethyl-4-(2-fluorobenzyl)-1-piperazinyl)-3-trifluoromethylsulfonyloxybenzyl)-N,N-diethylbenzamide (610 mg), as a yellow oil, which was used without further purification. The oil was dissolved in ethanol (7 mL) and aqueous 2.5 M (10%) sodium hydroxide solution (5 mL, 12.5 mmol) was added. The reaction mixture was set aside at room temperature for 5 h, then the ethanol removed by evaporation. The oily suspension of the sodium salt was clarified by the addition of water (5 mL), and the pH of the solution adjusted to 9-10 by the passage of gaseous carbon dioxide (from dry ice). The copious white precipitate was washed well with water and dried under vacuum (2 mm Hg) at room temperature overnight to yield the title compound as a white solid (431 mg, 85.6%). Calc. for $C_{31}H_{38}FN_3O_2$: C, 73.93; H, 7.61; N, 8.34; F, 3.77. Found C, 73.96; H, 7.67; N, 8.29; F, 3.75%. $^1$H NMR (CDCl$_3$, 300 MHz); δ 1.05 (d, J=6.1 Hz, 3H); 1.09 (d, J=6 Hz, 3H); 1.12 (br m, 3H); 1.24 (br m, 3H); 1.96 (t, J=10 Hz, 1H); 2.07 (t, J=10 Hz, 1H); 2.56 (br m, 2H); 2.60 (d, J=11 Hz, 1H); 2.72 (d, J=11 Hz, 1H); 3.29 (br m, 2H); 3.36 (d, J=14 Hz, 1H); 3.55 (br m, 2H); 3.89 (d, J=14 Hz, 1H); 5.13 (s, 1H); 6.57 (s, 1H); 6.66 (d, J=10 Hz, 2H); 7.00 (t, J=9 Hz, 1H); 7.07 (t, J=7.5 Hz, 1H); 7.10 (t, J=8 Hz, 1H); 7.20 (m, 1H); 7.27 (d, J=8 Hz, 2H); 7.38 (t, J=7 Hz, 1H); 7.43 (d, J=7 Hz, 2H).

Example 3 (Formula (iii))

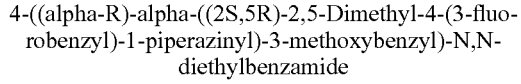

4-((alpha-R)-alpha-((2S,5R)-2,5-Dimethyl-4-(3-fluorobenzyl)-1-piperazinyl)-3-methoxybenzyl)-N,N-diethylbenzamide Benzotriazole (22.3 g, 187.5 mmol), 4-formyl-N,N-diethylbenzamide (38.5 g, 187.5 mmol, from Example 1), and (2R,5S)-1-allyl-2,5-dimethylpiperazine (28.9 g, 187.5 mmol, Chirotech Division of Dowpharma, The Dow Chemical Company, Cambridge, England) were added to toluene (2000 mL) in a 5 L flask with condenser and Dean-Stark trap. The reaction was heated at reflux with removal of water for 2-3 hours and distillation was continued to reduce the reaction volume to approximately 600 mL. The resulting mixture was cooled to room temperature, 800 mL of anhydrous tetrahydrofuran was added, and the solution was cooled to 0° C. The solution was stirred at 0° C. during slow addition of 300 mL of 1.0 M 3-methoxyphenylmagnesium bromide (300 mmol, Aldrich Chemical). The reaction was allowed to warm to room temperature and stirring was continued for 1.5 hours. Saturated ammonium chloride solution (90 mL) was added with stirring, followed by 100 g of anhydrous magnesium sulfate. After 1 hr the suspension was filtered, washing with 300 mL of tetrahydrofuran. The filtrate was concentrated to dryness, redissolved in 2000 mL of ethyl acetate, and washed sequentially with 1 M sodium hydroxide (4×800 mL), water (3×1000 mL) and saturated sodium chloride (500 mL). The ethyl acetate solution was dried over anhydrous sodium sulfate and the solvent was removed under vacuum to give a brown oil. Ethyl acetate was added to the oil with swirling until a mobile solution was obtained. Seed crystals of the desired product were added to catalyze crystallization. The resulting crystals were collected by filtration to give 21.01 g. Subsequent concentration and crystallization of mother liquors gave two additional crops of crystals (3.70 g and 4.94 g) for a total of 29.65 g (35%) of 4-((alpha-R)-alpha-((2S,5R)-4-allyl-2,5-dimethyl-1-piperazinyl)-3-methoxybenzyl)-N,N-diethylbenzamide.

The foregoing intermediate 22.48 g, 50.0 mmol) was dissolved in 100 mL of anhydrous tetrahydrofuran with 9.25 g (60 mmol) of thiosalicylic acid under nitrogen. A solution of bis(benzylideneactone)palladium (1.44 g, 2.5 mmol) and 1,4-bis(diphenylphosphino)butane (1.07 g, 2.5 mmol) in tetrahydrofuran (20 mL) was added and the reaction was stirred at room temperature for 2 hrs. The solvent was removed under vacuum. The residue was redissolved in a mixture of ethyl acetate (120 mL) and diethyl ether (250 mL) and washed with aqueous 2% sodium carbonate (3×200 mL) and water (2×100 mL). The organic layer was diluted with 800 mL of pentane and extracted three times with (50 mL of 1 M hydrochloric acid followed by 50 mL of water). The combined 300 mL of aqueous solution was filtered to remove suspended matter and made basic (pH ~12) with 5 M sodium hydroxide. The resulting oily suspension was extracted with dichloromethane (3×150 mL) and the extracts were dried over anhydrous sodium sulfate. Removal of solvent under vacuum gave 18.975 g of 4-((alpha-R)-alpha-((2S,5R)-2,5-dimethyl-1-piperazinyl)-3-methoxybenzyl)-N,N-diethylbenzamide as a glassy foam that was used without further purification.

Sodium iodide (45 mg, 0.3 mmol) was added to a solution of the foregoing intermediate (1.23 g, 3.00 mmol) in 15 mL of acetonitrile under nitrogen. Triethylamine (1.5 mL, 10.8 mmol) and 3-fluorobenzyl bromide (736 µL, 6.0 mmol) were added and the reaction was stirred overnight at room temperature. Solvent was removed under vacuum and saturated sodium bicarbonate (10 mL) was added to the residue. The resulting suspension was extracted with ethyl acetate (3×40 mL), the solvent was dried over anhydrous sodium sulfate, and the solvent was removed under vacuum to give 1.82 g of gummy residue. This material was purified by chromatography on silica gel (Biotage 4×15 cm column) with ethyl acetate to give the product as a yellow oil which crystallized upon titration with pentane (5 mL). Filtration and drying afforded 1.252 g of 4-((alpha-R)-alpha-((2S,5R)-2,5-dimethyl-4-(3-fluorobenzyl)-1-piperazinyl)-3-methoxybenzyl)-N,N-diethylbenzamide as a white solid. Calc. for $C_{32}H_{40}FN_3O_2$: C, 74.24; H, 7.79; N, 8.12; F, 3.67. Found C, 74.29; H, 7.84; N, 8.12; F, 3.58. $^1$H NMR (CDCl$_3$, 300 MHz); δ d1.08 (d, J~6 Hz, 3H); 1.10 (d, J~7 Hz, 3H); 1.23 (brd m, 6H); 1.99 (m, 2H); 2.6 (m, 4H); 3.18 (half of ABq, J~14 Hz, 1H); 3.28 (brd m, 2H); 3.54 (brd m, 2H); 3.79 (s, 3H); 3.87 (half of ABq, J~14 Hz, 1H); 5.10 (s, 1H); 6.7-7.0 (m, 4H); 7.06 (brd s, 2H); 7.1-7.35 (m, 4H); 7.46 (m, 2H).

Example 4 (Formula (iv)

4-((alpha-R)-alpha-((2S,5R)-2,5-Dimethyl-4-(2-fluorobenzyl)-1-piperazinyl)-3-methoxybenzyl)-N,N-diethylbenzamide By a procedure essentially identical to that of Example 3, the title compound was prepared from 1.23 g (3.00 mmol) of 4-((alpha-R)-alpha-((2S,5R)-2,5-dimethyl-1-piperazinyl)-3-methoxybenzyl)-N,N-diethylbenzamide, 2-fluorobenzyl bromide (724 µL, 6.0 mmol), sodium iodide (45 mg, 0.30 mmol), and triethylamine (1.51 mL, 10.8 mmol). The crude product was slurried with 1:1 saturated sodium carbonate/water for several hours with manual crushing of suspended solids. Crystalline product was collected by filtration, washed with water and dried to give 1.494 g of 4-((alpha-R)-alpha-((2 S,5R)-2,5-dimethyl-4-(2-fluorobenzyl)-1-piperazinyl)-3-methoxybenzyl)-N,N-diethylbenzamide as a white solid. Calc. for $C_{32}H_{40}FN_3O_2$ 0.1 $H_2O$: C, 73.99; H, 7.80; N, 8.09; F, 3.66. Found C, 73.98; H, 7.86; N, 8.00; F, 3.77. $^1$H NMR (CDCl$_3$, 300 MHz); δ □1.09 (d, J~7 Hz, 3H); 1.11 (d, J~7 Hz, 3H); 1.945 (apparent t, J~9 Hz, 1H); 2.07 (apparent t, J~9 Hz, 1H); 2.59 (m, 2H); 2.63 (d, J 11 Hz, 1H); 2.73 (d, J 11 Hz, 1H); 3.28 (brd m, 2H); 3.33 (half of ABq, J~14 Hz, 1H); 3.54 (brd m, 2H); 3.78 (s, 3H); 3.88 (half of ABq, J~14 Hz, 1H); 5.14 (s, 1H); 6.74 (s, 1H); 6.80 (m, 2H); 7.00 (t, J~8 Hz, 1H); 7.07 (t, J~7 Hz, 1H); 7.22 (m, 2H); 7.29 (half of ABq, J~8 Hz, 2H); 7.37 (t, J~7 Hz, 1H); 7.47 (half of ABq, J~8 Hz, 2H).

The following examples demonstrate the results from tests designed to demonstrate the utility of novel delta-receptor agonists, acting at a non-dopaminergic therapeutic target, in the treatment of parkinsonian symptoms. Several compounds have been identified that show oral activity in rodent models of Parkinson's disease. They produce clear beneficial effects, alleviating the motor impairments of rats treated with reserpine or haloperidol, without the significant safety issues associated with SNC80 or the dyskinesia side-effect profile of dopamine replacement therapy.

Example 5

The basic pharmacology of the Formulas (i)-(iv) is described below in terms of receptor binding affinity (delta and mu receptors from rat whole brain homogenate; kappa receptors from guinea pig cerebellar homogenate), intrinsic activity in mouse isolated vas deferens (delta receptor) and guinea pig isolated ileum (mu receptor). The following compounds were tested and compared to known results of SNC80.

Formula (i)

4-((alpha-R)-alpha-((2S,5R)-2,5-Dimethyl-4-(3-fluorobenzyl)-1-piperazinyl)-3-hydroxybenzyl)-N,N-diethylbenzamide Formula (ii)

4-((alpha-R)-alpha-((2S,5R)-2,5-Dimethyl-4-(2-fluorobenzyl)-1-piperazinyl)-3-hydroxybenzyl)-N,N-diethylbenzamide Formula (iii)

4-((alpha-R)-alpha-((2S,5R)-2,5-Dimethyl-4-(3-fluorobenzyl)-1-piperazinyl)-3-methoxybenzyl)-N,N-diethylbenzamide Formula (iv)

4-((alpha-R)-alpha-((2S,5R)-2,5-Dimethyl-4-(2-fluorobenzyl)-1-piperazinyl)-3-methoxybenzyl)-N,N-diethylbenzamide The above compounds were evaluated for in vitro opioid receptor affinity and activity in various receptor systems, including mouse vas deferens (Mouse Vas Deferens ED$_{50}$). The assay procedures used for such determinations of receptor activity are set out below.

Radioligand Binding:

Membrane fractions were incubated with test compound or naloxone (1×10$^{-6}$ M) plus 0.1 nM of the delta-opioid receptor agonist [$^3$H] DPDPE (specific activity 50.6 Ci/mmol), 0.1 nM of the mu-opioid receptor agonist [$^3$H]

DAMGO (specific activity 50.0 Ci/mmol) or 0.1 nM of the kappa-opioid receptor agonist [$^3$H]U69593 (specific activity 41.4 Ci/mmol) in 2 ml of 10 mM Tris-HCl buffer containing 5 mM MgCl$_2$ and protease inhibitors. Incubation was carried out for 90 min at 25° C. in order to permit the complete equilibration of the radioligand with its receptor. The reaction was terminated by rapid filtration through Whatman GF/C glass fiber filters using a cell harvester (model M-48R, Brandel Instruments, Gaithersberg, Md.) followed by two 5 ml rinses with ice-cold 50 mM Tris buffer. Non-specific binding was defined as that radioligand bound in the presence of 1×10$^{-6}$ M naloxone. Filters were counted by liquid scintillation spectrometry (LS 6500, Beckman Coulter Inc., Fullerton Calif.) at an efficiency, determined by external standards, of 40 to 45%.

Intrinsic Activity

Mouse Vas Deferens Studies:

Tension development in isolated mouse vas deferens was measured as described previously (Chang et al., 1993). Following cervical dislocation, vasa deferentia were isolated from male CD-1 mice (Charles River, Raleigh, N.C.) weighing 20-25 g. Muscles were suspended in individual organ baths containing Mg-free Krebs-Henseleit solution (37° C., aerated with O$_2$—CO$_2$, 95:5) of the following composition (mM): NaCl, 117.5; KCl, 4.75; CaCl$_2$, 2.6; KH$_2$PO$_4$, 1.2; NaHCO$_3$, 24.5; and glucose, 11. The vas deferens segments were positioned between platinum electrodes (Radnoti Glassware Technology Inc., Monrovia, Calif.) and connected to a Grass (Grass-Telefactor, West Warwick, R.I.) FTO3 isometric force transducer under a resting tension of 0.5 g. Muscles were stimulated to contract by administering 400 msec pulse trains (1 msec duration, supramaximal voltage, 10 Hz) with a Grass S88 stimulator. An IC$_{50}$ value for test compound inhibition of electrically-induced contractions was produced through the addition of cumulative concentrations of test compound to the bathing solution (Chang et al., 1993).

Guinea Pig Ileum Studies:

Tension developed in response to electrical stimulation of guinea pig isolated ileum was recorded as described previously by Gengo et al. (2003a). Male albino guinea pigs (Charles River, Raleigh, N.C.) weighing 300-500 g were euthanized by decapitation and an 8 cm section of ileum removed and divided into 2-3 cm segments. Individual segments were suspended in standard organ baths (Radnoti) and continuously bathed in Krebs-Henseleit solution (37° C., aerated with O$_2$/CO$_2$ 95:5) of the following composition: 117.5 mM NaCl, 4.75 mM KCl, 2.4 mM CaCl$_2$, 1.2 mM KH$_2$PO$_4$, 1.2 mM MgSO$_4$, 24.5 mM NaHCO$_3$, and 11 mM glucose. Tissues were suspended from Grass FTO3 isometric force transducers under a resting tension of 1 g and contractions were elicited by a field stimulation of 0.1 Hz pulses of 0.5 ms duration at supramaximal voltage using platinum electrodes and a Grass S88 stimulator. Test compound effects on electrically-induced contractions of the ileum were examined through the addition of cumulative concentrations of test compound to the bathing solution. The maximum concentration tested was limited by the solubility of the compound in these assay conditions.

Figure 2:
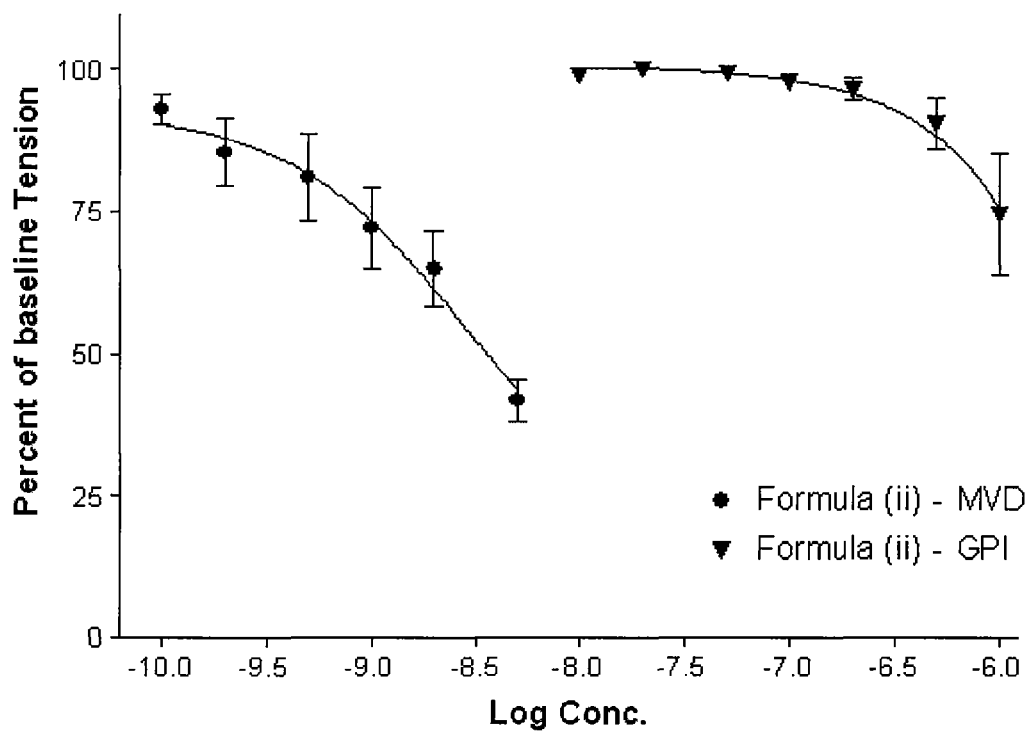
FIG. 2 shows the effects of Formula (ii) on electrically-induced contractions of mouse isolated vas deferens or guinea pig isolated ileum.

The percentage inhibition of the electrically induced muscle contractions was determined for the compounds at varying cumulative concentrations. The ED$_{50}$ values for formula (ii) were extrapolated from curves showing the dose concentration plotted against the response and are presented in FIG. 2.

The results are shown below in Table 1

TABLE 1

Binding and Intrinsic activity of Candidate Compounds

| Compound | Receptor Binding Affinity, Ki | | | Intrinsic Activity, EC$_{50}$ | |
|---|---|---|---|---|---|
| | Delta | Mu | Kappa | Delta (MVD) | Mu (GPI) |
| Formula (i) | 0.73 nM | 11.6 nM | 567 nM | 2.6 nM | 4540 nM |
| Formula (ii) | 0.77 nM | 7.8 nM | 171 nM | 3.0 nM | >1000 nM |
| Formula (iii) | 5.6 nM | 5000 nM | 100 nM | 29 nM | >1000 nM |
| Formula (iv) | 4.2 nM | 5000 nM | 100 nM | 4.1 nM | >1000 nM |
| SNC80 | 2.2 nM | 4800 nM | 4100 nM | 6.4 nM | >1000 nM |

Formulas (i-iv) clearly have high binding affinity for the delta receptor, and good intrinsic activity in the mouse isolated vas deferens—indicating agonist activity that is selective for the delta receptor. Notably, Formula (i) and (ii) have increased binding affinity for the delta and mu receptors when compared to SNC80.

Example 6

Behavioral parameters were monitored in transparent shoebox cages that measured 45×25×20 cm, with a 1-cm depth of wood chips on the cage floor and a plastic grid on top of the cage. Rectangular photocell monitors with a bank of 3 photocell beams surrounded each test cage. Ambulations (locomotor activity: total number of beam breaks in 1 hour) were recorded by computer and stored for each test session.

Animals were administered injections of dextrose, reserpine or haloperidol. Formula (i) or Formula (ii) was then administered 18 hours after reserpine at doses of 3, 10 or 30 mg/kg or 15 minutes after haloperidol at doses of 1, 3, 10 or 30 mg/kg. Animals were monitored over a 60-min period in all instances, and data are expressed as total counts over the entire 1 h test period. Group sizes and model validity was defined using the published delta agonist of effect, SNC80. In these studies, clinically effective therapies such as dopamine replacement therapy restore locomotor activity in dopamine-depleted or dopamine antagonist treated animals. Dopamine replacement therapy also, however, produces an overshoot in locomotor activity beyond the locomotor counts observed with normal control animals (with intact dopamine systems). This is considered the activating component of dopamine replacement therapy that results in dyskinesias in Parkinson's patients.

SNC80, Formula (i) and Formula (ii) demonstrated clear efficacy in the haloperidol and reserpine treated rat models of Parkinson's disease. FIG. 1 shows that Formula (i) and (ii) are potent compounds in both the reserpine (FIG. 1B) and haloperidol treated animal rat models (FIG. 1C) and clearly reduced the effects of the haloperidol and reserpine by increasing locomotor activity. Critically, neither Formula (i) nor Formula (ii) produced increases in locomotor activity beyond that of normal control animals (with intact dopamine systems (FIG. 1A), suggesting no (or very little) propensity to produce dyskinesias in Parkinson's disease patients In the top graph of FIG. 1, the dextrose/dextrose condition indicates the locomotor activity of normal rats in these light-beam boxes. The three-beam boxes used in the screening model gives a simple measure of gross ambulation. The return to normal activity reported previously with SNC80 (Hille et al, 2001) includes coordinated fine motor movements recorded as part of general activity in a 48 beam box (but not detected in the 3 beam box). Clearly, Formula (ii) provides the level of locomotor activity as SNC80 without the level of negative effects relating to seizure activity.

FIG. 3 shows that Formula (ii) shows potency following both intraperitoneal injection and oral dosing (by gavage). Oral activity is a distinct advantage in a new Parkinson's therapy because currently acceptable therapeutics for Parkinson's disease are not usually delivered by gastric absorption.

Figure 4:
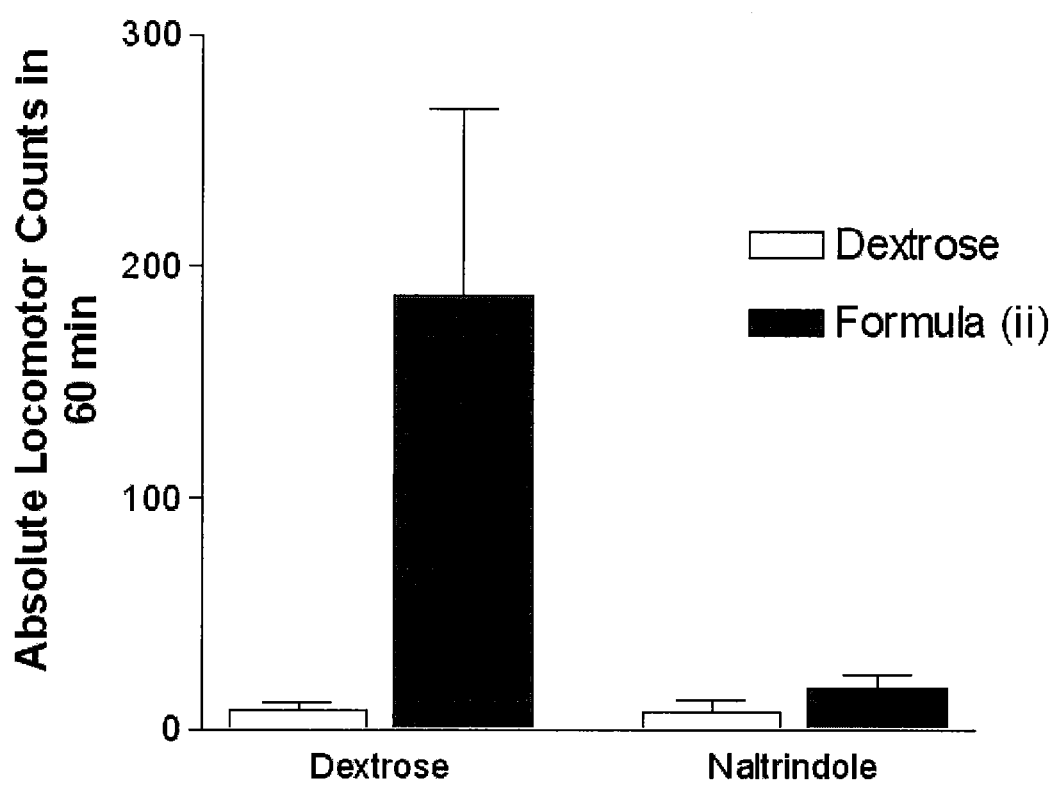
FIG. 4 shows the results of blockage by Naltrindole of the beneficial results of Formula (ii).

The delta mechanism of action of the candidate compound Formula (ii) was supported by the use of the delta receptor antagonist naltrindole (NTI) with the results set forth in FIG. 4. Naltrindole completely blocked the beneficial effects of Formula (ii) in haloperidol treated rats while naltrindole alone had no effect in this model (FIG. 4).

Example 7

One of the most obvious side-effects of potent delta agonists that rapidly penetrate the blood brain barrier is convulsive episodes reminiscent of possible seizure-like brain activity. The mouse is the chosen species for study of these effects since the mouse is the most highly convulsion-sensitive rodent species and mice present with a clear and obvious, whole body tonic-clonic convulsion. One of the earliest phases of delta agonist safety assessments is thus the determination of the convulsion threshold in mice. While SNC80 is a delta agonist that produces beneficial effects in rodent and primate models of Parkinson's disease, its clinical utility is limited by its low convulsion threshold in rodents.

Both Formula (i) and Formula (ii) demonstrate similar beneficial effects as SNC80 in rodent models of Parkinson's disease at doses in the range of 1-30 mg/kg (Example 6 above and FIGS. 1 B and C). Formula (i) showed some seizure-like convulsant activity in mice at oral doses of 15 mg/kg and higher (Table 2) but showed no oral-seizure-like convulsant activity in rats testing (results not shown), which are clearly a different animal model, at oral doses up to 40 mg/kg. Formula (ii) showed seizure-like convulsant activity in mice at oral doses of 15 mg/kg and higher (Table 2). Importantly, the seizure activity of Formula (i) and (ii) in mice is reduced relative to SNC80.

TABLE 2

Seizure-like convulsion incidence in mice (% of animals treated)

| Compound | Intravenous (mg/kg) | | | Oral (mg/kg) | | | |
|---|---|---|---|---|---|---|---|
| | 0.3 | 1 | 3 | 15 | 30 | 60 | 100 * |
| SNC80 | 0% | 30% | 100% | Not orally active | | | |
| Formula (i) | 0% | 50% | 40% | 23% | | | |
| Formula (ii) | | 0% | 30% | 20% | 20% | 30% | |
| Formula (iii) | | | | | 20% | | 0% |
| Formula (iv) | | 0% | 20% | | 0% | | 10% |

* dose level limited by solubility in 5% dextrose for mouse dosing at 1 ml/kg

From the above results (Examples 5 through 7) it is apparent that Formula (i) and (ii) have the following characteristics providing advantageous effects over the currently published delta agonist (SNC80) and/or dopamine replacement therapy:

1. An opioid receptor agonist selective for the delta receptor.
2. Active in Parkinson's disease rodent models.
   a. Potent at improving locomotor activity of haloperidol-treated rats.
   b. Potent at improving locomotor activity in reserpine treated rats.
3. Orally active in Parkinson's disease rodent models.
   a. As contrasts the lack of oral activity observed with the existing delta agonist with demonstrated activity in these assays, SNC80.
4. No evidence for overshoot of locomotor activation, implying no propensity to induce dyskinesias associated with dopamine replacement therapy.

While the invention has been described herein in reference to specific aspects, features and illustrative embodiments of the invention, it will be appreciated that the utility of the invention is not thus limited, but rather extends to and encompasses numerous other aspects, features and embodiments. Accordingly, the claims hereafter set forth are intended to be correspondingly broadly construed, as including all such aspects, features and embodiments, within their spirit and scope.

REFERENCES

The contents of the following references are hereby incorporated by reference herein for all purposes.

Broom D C, Jutkiewicz E M, Folk J E, Traynor J R, Rice K C, Woods J H, (2002), Nonpeptidic delta-opioid receptor agonists reduce immobility in the forced swim assay in rats. *Neuropsychopharmacology* 26(6):744-755.

Chang K J, Rigdon G C, Howard J L and McNutt R W, (1993), A novel, potent and selective nonpeptidic delta opioid receptor agonist BW373U86. *J Pharmacol Exp Ther* 267(2):852-857.

Cormr S D, Hoenicke E M, Sable A I, McNutt R W, Chang K J, De Costa B R, Mosberg H I and Woods J H (1993) Convulsive effects of systemic administration of the delta opioid agonist BW373U86 in mice. *J Pharmacol Exp Ther* 267(2):888-895.

Cuello C A, Paxinos G, (1978) Evidence for a long leu-enkephalin striopallidal pathway in rat brain. *Nature* 271:178-180

De Ceballos M L, Fernandez A, Jenner, Marsden C D, (1993) Parallel alterations in Met-enkephalin and substance P levels in medial globus pallidus in Parkinson's disease patients. *Neurosci. Lett.* 160:163-166

Gerfen C R, Young Ws 3$^{rd}$, (1988) Distribution of striatonigral and striatopallidal peptidergic neurons in both patch and matrix compartments: An in situ hybridization histochemistry and fluorescent retrograde tracing study. *Brain Res.* 460:161-167

Henry B, Brotchie J M, (1996) Potential of opioid antagonists in the treatment of levodopa-induced dyskinesias in Parkinson's disease. *Drugs Aging* 9:149-158

Henry B, Fox S H, Crossman A R, and Brotche, J M, (2001) Mu ☐and delta-opioid receptor antagonist reduce levodopa-induced dyskinesia in the MPTP-lesioned primate model of Parkinson's disease. *Experimental Neurology* 171:139-146

Hill M P, Hille C J, Brotchie J M, (2000) δ opioid receptor agonists as a therapeutic approach in Parkinson's disease. *Drugs News Perspect.*13(5):261-268

Hille C J, Fox S H, Maneuf Y P, Crossman A R, Brotchie J M, (2001) Antiparkinsonian action of a δ opioid agonist in rodent and primate models of Parkinson's disease. *Exp. Neurol.* 172:189-198

Herrero M T, Augood S J, Hirsch E C, Javoy-Agid F, Luquin M R, Agid Y, Obeso J A, Emson P C, (1995) Effects of L-DOPA on preproenkephalin and preprotachykinin gene expression in MPTP-treated monkey striatum. *Neurosci.* 68:1189-1198

Jolkkonen J, Jenner O, Marsden C D, (1995) L-DOPA reverses altered gene expression of substance P but not enkephalin in the caudate-putamen of common marmosets treated with MPTP. *Brain Res. Mol. Brain Res.* 32:297-307

Maneuf Y P, Mitchell I J, Crossman A R, Brotchie J M, (1994) On the role of enkephalin cotransmission in the GABAergic striatal efferents to the globus pallidus. *Exp. Neurol.* 125:65-71

Negus S S, Gatch M B, Mello N K, Zhang X, Rice K (1998) Behavioral effects of the delta-selective opioid agonist SNC80 and related compounds in rhesus monkeys. *J. Pharmacol. Exp. Ther.,* 286: 362-75

Negus S S, Mello N K, Portoghese P S, Lukas S E, Mendelson J H, (1995) Role of delta opioid receptors in the reinforcing and discriminative stimulus effects of cocaine in rhesus monkeys. *J. Pharmacol. Exp. Ther.,* 273: 1245-56

Negus S S, Butelman E R, Chang K-J, DeCosta B, Winger G, Woods J H, (1994) Behavioral effects of the systemically active delta opioid agonist BW373U86 in rhesus monkeys. *J. Pharmacol. Exp. Ther.,* 270, 1025-34

Nisbet A P, Foster O J, Kingsbury A, Eve D J, Daniel S E, Marsden C D, Lees A J, (1995) Perproenkephalin and preprotachykinin messenger RNA expression in normal human basal ganglia and in Parkinson's disease. *Neurosci.* 66:361-376

Silverdale M A, Fox S H, Crossman A R, Brotchie J M, (2003) Potential nondopaminergic drugs for Parkinson's disease. *Parkinson's Disease: Advances in Neurology* 91:273-291

That which is claimed is:

1. A transdermal patch affixable to a corporeal locus, comprising a composition for treating Parkinson's disease in a subject experiencing same, the composition consisting of Levodopa and at least one diarylmethylpiperazine compound of formula selected from the group consisting of:

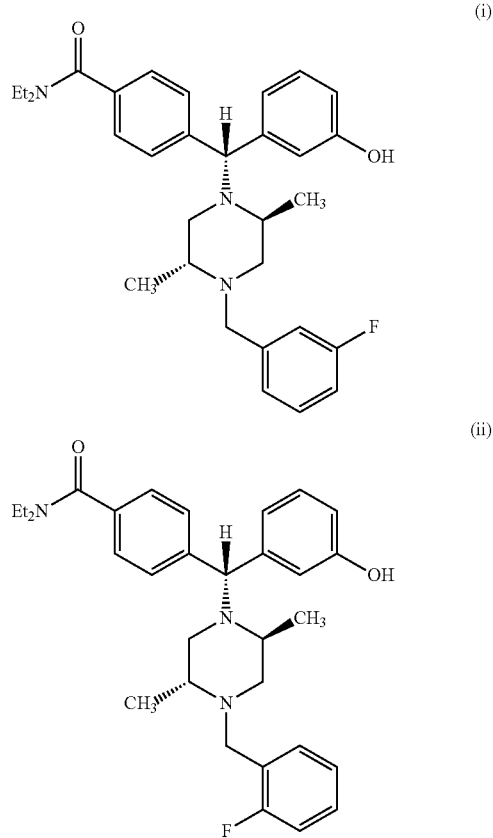

and pharmaceutically acceptable esters and salts wherein the compound of formula (i) or formula (ii) is present in an effective amount to treat Parkinson's disease thereof, wherein the diarylmethylpiperazine compound exhibits delta opioid receptor agonist and mu opioid receptor antagonist activity.

* * * * *